United States Patent [19]

Janssens et al.

[11] Patent Number: 4,826,848

[45] Date of Patent: May 2, 1989

[54] ANTIDEPRESSIVE SUBSTITUTED N-[(4-PIPERIDINYL)ALKYL] BICYCLIC CONDENSED OXAZOL- AND THIAZOLAMINES

[75] Inventors: Frans E. Janssens, Bonheiden; Theophilus T. J. M. Van Offenwert, Vosselaar; Raymond A. Stokbroekx, Beerse, all of Belgium; Bernard R. Boar, Greenford, United Kingdom

[73] Assignee: Janssen Pharmaceutica N.V., Beerse, Belgium

[21] Appl. No.: 156,379

[22] Filed: Feb. 16, 1988

Related U.S. Application Data

[60] Division of Ser. No. 45,936, Jun. 23, 1987, Pat. No. 4,749,702, which is a division of Ser. No. 833,710, Feb. 27, 1986, Pat. No. 4,689,330, which is a continuation-in-part of Ser. No. 723,400, Apr. 15, 1985, abandoned.

[51] Int. Cl.$^4$ .................. A61K 31/505; C07D 513/04
[52] U.S. Cl. ..................................... 514/258; 544/255
[58] Field of Search ....................... 544/255; 514/258

[56] References Cited

U.S. PATENT DOCUMENTS

| | | | |
|---|---|---|---|
| 3,953,461 | 4/1976 | Denzel et al. | 546/114 |
| 4,224,333 | 9/1980 | Clemence et al. | 546/197 X |
| 4,342,761 | 8/1982 | Ward | 546/198 X |

OTHER PUBLICATIONS

*Burger's Medicinal Chemistry,* Fourth Edition, Part III, Manfred E. Wolff (Ed.), pp. 943–944, John Wiley, New York, 1981.

Colpaert, F. et al., *Drug Development Research* vol. 8, pp. 361–371 (1986).

*Primary Examiner*—Richard A. Schwartz
*Attorney, Agent, or Firm*—David J. Levy

[57] ABSTRACT

Novel substituted N-[(4-piperidinyl)alkyl] bicyclic condensed oxazol- and thiazolamines useful as anti-depressives, in the treatment of Parkinson's disease and in the treatment of diseases related with disturbed enterokinesia.

20 Claims, No Drawings

ANTIDEPRESSIVE SUBSTITUTED N-[(4-PIPERIDINYL)ALKYL] BICYCLIC CONDENSED OXAZOL- AND THIAZOLAMINES

CROSS-REFERENCE TO RELATED APPLICATIONS

This is a division of U.S. Ser. No. 45,936 filed June 23, 1987, now U.S. Pat. No. 4,749,702, which is a division of U.S. Ser. No. 833,710 filed Feb. 27, 1986, now U.S. Pat. No. 4,689,330 issued Aug. 27, 1987 which is a continuation-in-part of our application Ser. No. 723,400, filed April 15, 1985 now abandoned.

BACKGROUND OF THE INVENTION

In U.S. Pat. No. 4,219,559 there are described a number of N-heterocyclyl-4-piperidinamines, wherein said heterocyclyl is imidazole being condensed with benzene or pyridine, which compounds are useful as antihistaminic agents.

The compounds of the present invention, containing an analogous heterocyclic radical being substituted on a piperidine moiety, differ therefrom essentially by the fact that said heterocyclyl is oxazole or thiazole being condensed with benzene, pyridine or pyrimidine and by their unexpected pharmacological properties.

DESCRIPTION OF THE PREFERRED EMBODIMENTS

The present invention is concerned with novel substituted N-[(4-piperidinyl)alkyl]bicyclic condensed oxazol- and thiazolamines which may structurally be represented by the formula

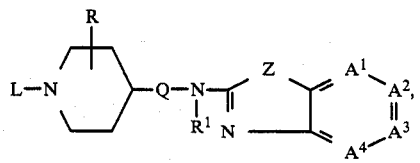

the pharmaceutically acceptable acid addition salts and the stereochemically isomeric forms thereof, wherein $=A^1-A^2=A^3-A^4=$ is a bivalent radical having the formula

 (a),

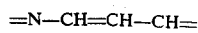 (b),

 (c),

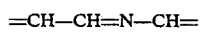 (d),

 (e),

 (f), or

 (g)

wherein one or two hydrogen atoms in said radicals (f)-(g) and up to three hydrogen atoms in said radicals (a)-(e), may each independently from each other be replaced by halo, hydroxy, amino, trifluoromethyl, $C_{1-6}$alkyl or $C_{1-6}$alkyloxy, or two hydrogen atoms in said radicals (a)-(e) substituted on adjacent carbon atoms may be replaced by a bivalent radical of formula $-O-CH_2-O-$ or $-O-CH_2-CH_2-O-$;

Z is $-O-$ or $-S-$;

$R^1$ is a member selected from the group consisting of hydrogen, $C_{1-6}$alkyl, $C_{1-6}$alkylcarbonyl, aryl $C_{1-6}$alkyl, arylcarbonyl and $C_{1-6}$alkyloxycarbonyl;

Q is $C_{1-4}$alkanediyl;

R is a member selected from the group consisting of hydrogen, $C_{1-6}$alkyl, hydroxy and $C_{1-6}$alkyloxy;

L is a member selected from the group consisting of a radical of formula

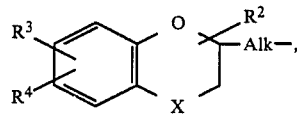 (h)

and a radical of formula

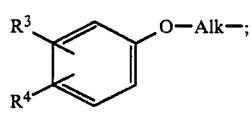 (i)

Alk is $C_{1-4}$alkanediyl;

X is $-O-$ or $-CH_2-$;

$R^2$ is hydrogen or $C_{1-6}$alkyl;

$R^3$ and $R^4$ are each independently selected from the group consisting of hydrogen, halo, trifluoromethyl, hydroxy, $C_{1-6}$alkyl, $C_{1-6}$alkyloxy and phenyl $C_{1-6}$alkyloxy;

wherein aryl is a member selected from the group consisting of phenyl, substituted phenyl, pyridinyl, mono- and di($C_{1-6}$alkyloxy)pyridinyl, thienyl, halothienyl, $C_{1-6}$alkylthienyl, pyrrolyl, $C_{1-6}$alkylpyrrolyl, furanyl, furanyl substituted with $C_{1-6}$alkyl, pyrazinyl, thiazolyl and imidazolyl; said substituted phenyl being phenyl substituted with up to 3 substituents each independently selected from the group consisting of halo, hydroxy, trifluoromethyl, $C_{1-6}$alkyl and $C_{1-6}$alkyloxy.

As used in the foregoing definitions the term halo is generic to fluoro, chloro, bromo and iodo; the term "$C_{1-6}$alkyl" is meant to include straight and branch chained saturated hydrocarbon radicals having from 1 to 6 carbon atoms such as, for example, methyl, ethyl, 1-methylethyl, 1,1-dimethylethyl, propyl, 2-methylpropyl, butyl, pentyl, hexyl and the like; "$C_{1-4}$alkanediyl" is meant to include bivalent straight or branch chained alkanediyl radicals having from 1 to 4 carbon atoms.

Preferred compounds within the invention are those wherein L is a radical of formula (h) wherein $R^3$ and $R^4$ are both hydrogen; or L is a radical of formula (i) wherein $R^3$ is hydrogen, halo, $C_{1-6}$alkyl, $C_{1-6}$alkyloxy or phenyl $C_{1-6}$alkyloxy and $R^4$ is hydrogen, halo or $C_{1-6}$alkyloxy.

Particularly preferred compounds are those preferred compounds wherein R is hydrogen; L is a radical of formula (h) wherein $R^2$ is hydrogen, or L is a radical of formula (i) wherein $R^3$ is hydrogen or halo and $R^4$ is hydrogen; and $R^1$ is a member selected from the group consisting of hydrogen, $C_{1-6}$alkyl, $C_{1-6}$alkylcarbonyl, aryl $C_{1-6}$alkyl and arylcarbonyl.

More particularly preferred compounds are those particularly preferred compounds wherein Q is $C_{1-3}$alkanediyl; L is a radical of formula (h) wherein Alk is methylene; and $R^1$ is a member selected from the group consisting of hydrogen, $C_{1-4}$alkyl, aryl $C_{1-2}$alkyl and arylcarbonyl, wherein aryl is a member selected from the group consisting of phenyl, substituted phenyl, furanyl and thiazolyl; said substituted phenyl being phenyl substituted with up to 2 substituents each independently selected from the group consisting of halo, hydroxy, trifluoromethyl, methyl and methoxy.

Those particularly preferred compounds wherein $=A^1-A^2=A^3-A^4=$ is a bivalent radical of formula (a) which may be substituted with up to three $C_{1-6}$alkyloxy radicals are especially preferred.

More especially preferred compounds are selected from the group consisting of N-[[1-[(2,3-dihydro-1,4-benzodioxin-2-yl)methyl]-4-piperidinyl]methyl]-2-benzothiazolamine, the pharmaceutically acceptable acid additions salts and the possible stereochemically isomeric forms thereof, whereby (S)-(−)-N-[[1-[(2,3-dihydro-1,4-benzodioxin-2-yl)methyl[-4-piperidinyl]methyl]-2-benxothiazolamine and the pharmaceutically acceptable acid additions salts thereof are most preferred.

In order to simplify the structural representations of the compounds of formula (I) and of certain precursors and intermediates thereof the

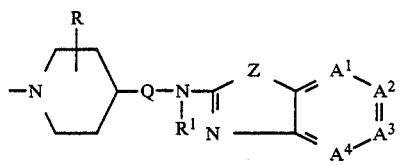

radical will hereafter be represented by the symbol D.

The compounds of formula (I) can generally be prepared by N-alkylating an intermediate of formula (III) with a reagent of formula (II).

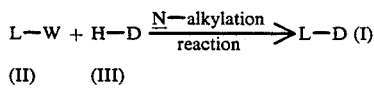

In (II) W represents an appropriate reactive leaving group such as, for example, halo, e.g., chloro, bromo or iodo, or a sulfonyloxy group, e.g. methylsulfonyloxy or 4-(methylphenyl)sulfonyloxy. The alkylation reaction is conveniently conducted in an inert organic solvent such as, for example, an aromatic hydrocarbon, e.g., benzene, methylbenzene, dimethylbenzene, and the like; a $C_{1-6}$alkanol, e.g., methanol, ethanol, 1-butanol and the like; a ketone, e.g., 2-propanone, 4-methyl-2-pentanone and the like; an ether, e.g., 1,4-dioxane, 1,1'-oxybisethane, tetrahydrofuran and the like; N,N-dimethylformamide (DMF); N,N-dimethylacetamide (DMA); dimethyl sulfoxide (DMSO); nitrobenzene; 1-methyl-2-pyrrolidinone; and the like. The addition of an appropriate base such as, for example, an alkali or an earth alkaline metal carbonate, hydrogen carbonate, hydroxide, and oxide, e.g., sodium carbonate, sodium hydrogen carbonate, potassium carbonate, sodium hydroxide, calcium carbonate, calcium hydroxide, calcium oxide and the like, or an organic base, such as, for example, a tertiary. amine, e.g., N,N-diethylethanamine, N-(1-methylethyl)-2-propanamine, 4-ethylmorpholine and the like may be utilized to pick up the acid which is liberated during the course of the reaction. In some circumstances the addition of a iodide salt, preferably an alkali metal iodide, is appropriate. Somewhat elevated temperatures may enhance the rate of the reaction.

The compounds of formula (I) can also be prepared by the reductive N-alkylation reaction of (III) with an appropriate carbonyl-compound of formula $L'=C=O$ (IV), said $L'=C=O$ being a compound of formula L—H wherein a —$CH_2$— radical is oxidated to a carbonyl radical.

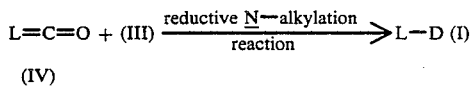

Said reductive N-alkylation reaction may conveniently be carried out by catalytically hydrogenating a stirred and heated mixture of the reactants in a suitable reaction-inert organic solvent according to art-known catalytic hydrogenating procedures. The reaction mixture may be stirred and/or heated in order to enhance the reaction rate. Suitable solvents are, for example, water; $C_{1-6}$alkanols, e.g. methanol, ethanol, 2-propanol and the like; cyclic ethers, e.g. 1,4-dioxane and the like; halogenated hydrocarbons, e.g. trichloromethane and the like; N,N-dimethylformamide; dimethyl sulfoxide and the like; or a mixture of two or more of such solvents. The term "art-known catalytic hydrogenating procedures" means that the reaction is carried out under hydrogen atmosphere and in the presence of an appropriate catalyst such as, for example, palladium-on-charcoal, platinum-on-charcoal and the like. In order to prevent the undesired further hydrogenation of certain functional groups in the reactants and the reaction products it may be advantageous to add an appropriate catalyst-poison to the reaction mixture, e.g., thiophene and the like.

The compounds of formula (I) can also be prepared by oxidatively cyclizing an urea or thiourea derivative of formula (V) in the presence of an appropriate oxidant.

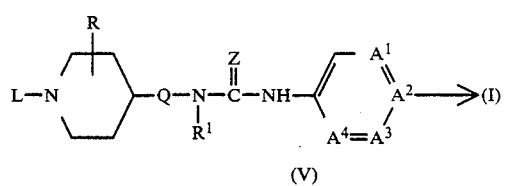

Appropriate oxidants are, for example, halogens, e.g. chlorine and bromine, thionyl chloride, sulfuryl chloride, thionyl bromide, sulfuryl bromide and the like agents. The said cyclization reaction is most conveniently conducted in a reaction-inert solvent such as, for example, an halogenated hydrocarbon, e.g. tetrachloromethane, trichloromethane and the like. Elevated temperatures may be appropriate to enhance the reaction rate.

The compounds of formula (I) can also be prepared by reacting a bicyclic condensed oxazol- or thiazol of formula (VII) with a piperidine of formula (VI), wherein $E^1$ and $E^2$ are selected so that during he reaction a radical —$NR^1$— is formed.

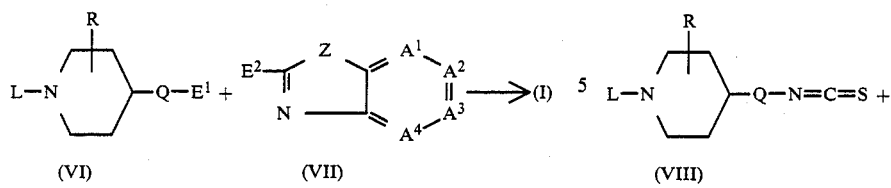

(VI)   (VII)

For example, the compounds of formula (I) can be prepared by reacting a piperidine of formula (VI) wherein $E^1$ is a radical of formula $-NR^1H$, said piperidine being represented by the formula (VI-a), with an intermediate of formula (VII) wherein $E^2$ is a radical of formula $-W^1$, said intermediate being represented by the formula (VII-a). In (VII-a) $W^1$ has the previously described meaning of W, but it may also be $C_{1-6}$alkyloxy, $C_{1-6}$alkylthio or $C_{1-6}$alkylsulfonyl.

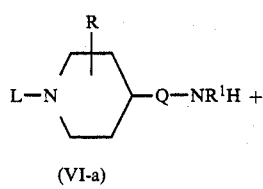

(VI-a)

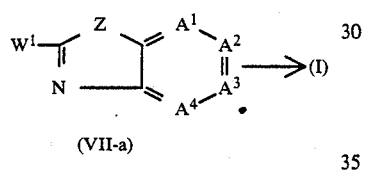

(VII-a)

Additionally, the compounds of formula (I) can be prepared by reacting a piperidine of formula (VI) wherein $E^1$ is W, said W having the previously described meaning, with an intermediate of formula (VII) wherein $E^2$ is a radical of formula $-NR^1H$.

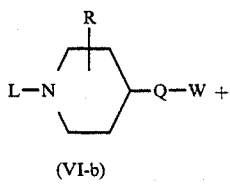

(VI-b)

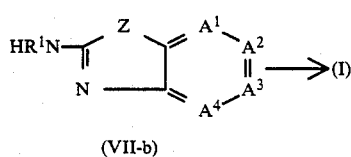

(VII-b)

Said N-alkylation reactions may carried out following the procedures described hereinabove for the preparation of (I) starting from (II) and (III).

The compounds of formula (I) wherein Z is O and $R^1$ is hydrogen, said compounds being represented by the formula (I-a), can also be prepared by cyclodesulfurizing an intermediate of formula (X), which may conveniently be formed in situ by condensing an isothiocyanate (VIII) with an aromatic aminoalcohol of formula (IX).

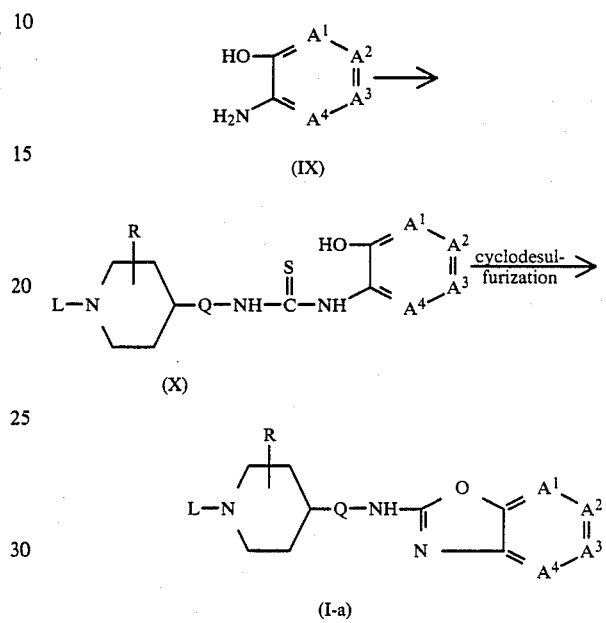

(VIII)

(IX)

(X)

(I-a)

Said cyclodesulfurization reaction may be carried out by the reaction of (X) with an appropriate alkyl halide, preferably iodomethane in a suitable reaction-inert organic solvent, e.g., a $C_{1-6}$alkanol such as, methanol, ethanol, 2-propanol and the like. Otherwise, the cyclodesulfurization reaction may be carried out by the reaction of (X) with an appropriate metal oxide or salt in an appropriate solvent according to art-known procedures. For example, the compounds of formula (I) can easily be prepared by the reaction of (X) with a Hg(II) or Pb(II) oxide or salt such as, for example, HgO, HgCl$_2$, Hg(OAc)$_2$, PbO or Pb(OAc)$_2$. In certain instances it may be appropriate to supplement the reaction mixture with a small amount of sulfur. Even so methanediimines, especially dicyclohexylcarbodiimide may be used as cyclodesulfurizing agents.

The compounds of formula (I) wherein $R^1$ is hydrogen, said compounds being represented by the formula (I-b), may be prepared by cyclizing an intermediate (XIII), which in situ may be formed by reacting an isocyanate or isothiocyanate (XI) with an aromatic amine (XII).

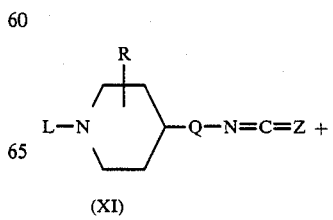

(XI)

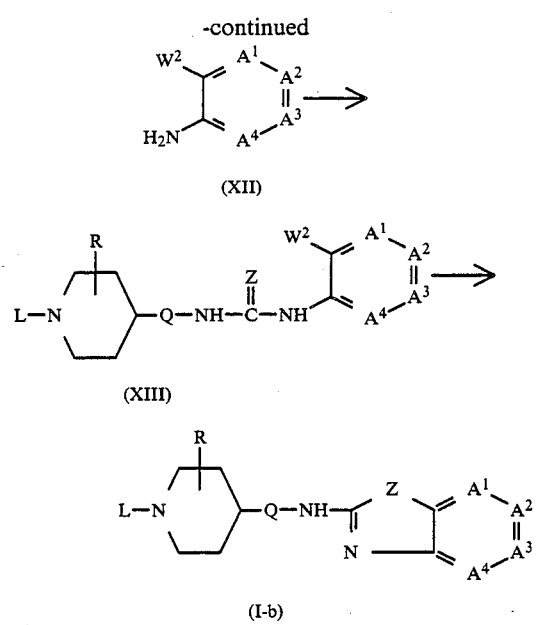

In (XII) and (XIII) $W^2$ represents an appropriate leaving group such as, for example, halo, e.g. chloro and bromo; $C_{1-6}$alkyloxy and $C_{1-6}$alkylthio.

The compounds of formula (I) wherein Alk contains at least two carbon atoms, said compounds being represented by formulae (I-c-1) and (I-c-2), may also be prepared by reacting an appropriate alkene of formula (XIV-a) or (XIV-b) respectively, with an intermediate of formula (III) by stirring and, if desired, heating the reactants together, preferably in a suitable solvent such as, for example, an alcohol, e.g., methanol, ethanol, 1-butanol and the like.

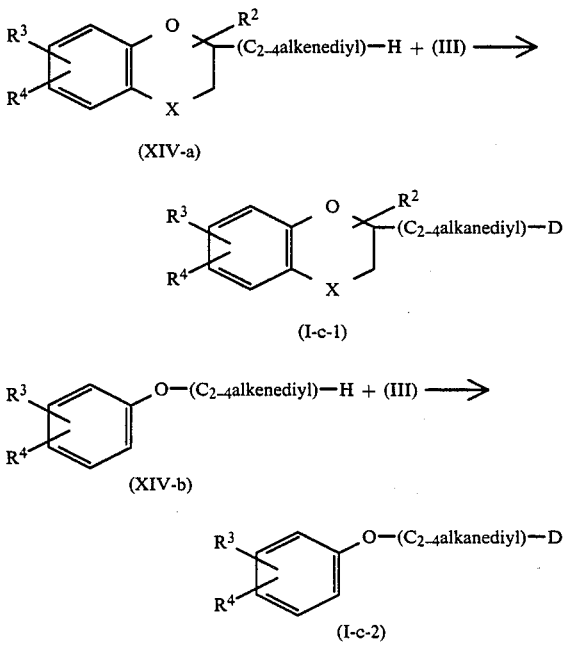

The compounds of formula (I) may also be converted into each other following art-known functional group transformation procedures. A number of such reactions will be described hereinafter in more detail.

The compounds of formula (I) wherein $R^1$ is hydrogen may be converted to the compounds of formula (I) wherein $R^1$ is other than hydrogen following art-known procedures such as, for example, N-alkylation, acylation, reductive N-alkylation and the like methods. A number of such procedures will be described hereinafter in more detail.

For example, $C_{1-6}$alkyl or aryl $C_{1-6}$alkyl groups may be introduced by reacting the starting compounds with an appropriate N-alkylating agent following the procedures described hereinabove for the preparation of (I) starting from (II) and (III), or by reacting the starting compounds with an appropriate carbonyl-compound following the reductive N-alkylation procedures described hereinabove for the preparation of (I) starting from (IV) and (III).

$C_{1-6}$Alkylcarbonyl or arylcarbonyl groups may be introduced by reacting the starting amine with an appropriate carboxylic acid or a reactive derivative thereof following art-known amidation reaction procedures. The carboxylic acid may be converted into a reactive derivative thereof such as, for example, an anhydride or a carboxylic acid halide, which subsequently, is reacted with the amine; or the amine may be reacted with an appropriate carboxylic acid and a suitable reagent capable of forming amides e.g. dicyclohexylcarbodiimide, 2-chloro-1-methylpyridinium iodide and the like.

$C_{1-6}$Alkyloxycarbonyl groups may be introduced by reacting the starting compounds of formula (I) wherein $R^1$ is hydrogen with, for example, a $C_{1-6}$alkyloxycarbonyl halogenide or the like reagents.

The compounds of formula (I) containing a substituted nitrogen atom may be converted into the corresponding compounds of formula (I) wherein said nitrogen bears a hydrogen atom following art-known methods for preparing N—H groups such as, for example, where said nitrogen is substituted with an aryl-$CH_2$- group, by treating the starting compounds with hydrogen in the presence of a suitable catalyst, e.g. palladium-on-charcoal, platinum-on-charcoal, in an appropriate solvent; or, where said nitrogen atom is substituted with an arylcarbonyl or $C_{1-6}$alkylcarbonyl or $C_{1-6}$alkyloxycarbonyl group by treating the starting compounds with an aqueous basic solution, e.g. an aqueous alkali metal hydroxide solution.

In all of the foregoing and in the following preparations, the reaction products may be isolated from the reaction mixture and, if necessary, further purified according to methodologies generally known in the art.

The compounds of formula (I) have basic properties and, consequently, they may be converted to their therapeutically active non-toxic acid addition salt forms by treatment with appropriate acids, such as, for example, inorganic acids, such as hydrohalic acid, e.g. hydrochloric, hydrobromic and the like, and sulfuric acid, nitric acid, phosphoric acid and the like; or organic acids, such as, for example, acetic, propanoic, hydroxyacetic, 2-hydroxy-propanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, benzoic, 2-hydroxybenzoic, 3-phenyl-2-propenoic, α-hydroxybenzeneacetic, 4-amino-2-hydroxybenzoic and the like acids. Conversely the salt form can be converted by treatment with alkali into the free base form.

A number of intermediates and starting materials in the foregoing preparations are known compounds which may be prepared according to art-known methodologies of preparing said or similar compounds. A number of such preparation methods will be described hereinafter in more detail.

The intermediates of formula (III) can conveniently be prepared by oxidatively cyclizing an urea or thiourea of formula (XVII) following the procedure described hereinabove for the preparation of (I) starting from (V), thus preparing a bicyclic condensed oxazole or thiazole of formula (XVI) and, if desired, subsequently N-alkylating (XVI), thus preparing an intermediate of formula (XV), followed by a deprotection reaction of (XV). The urea or thiourea derivative of formula (XVII) can be prepared by reacting a piperidine isocyanate or isothiocyanate (XXI) with an appropriate aromatic amine (XX) or alternatively, by reacting a piperidinamine (XIX) with an appropriate aromatic isocyanate or isothiocyanate (XVIII).

In the foregoing scheme, P is an appropriate protective group such as, for example, phenylmethyl, acetyl, ethoxycarbonyl and the like groups. The elimination of the protective group P in (XV) may generally be carried out following art-known procedures such as, for example, by hydrolysis in alkaline or acidic aqueous medium, or by katalytic hydrogenation.

The intermediates of formula (III) wherein Z is O, said intermediates being represented by the formula (III-a), may alternatively be prepared by cyclodesulfurizing a thiourea of formula (XXIII), which may in situ be formed by condensing an isothiocyanate of formula (XXII) with an aromatic alcohol (IX) following the procedures described hereinabove for the preparation of (I-a) starting from (VIII) and (IX), and, if desired, subsequently N-alkylating the thus obtained intermediate (XXIV) and eliminating the protective group P as described hereinabove.

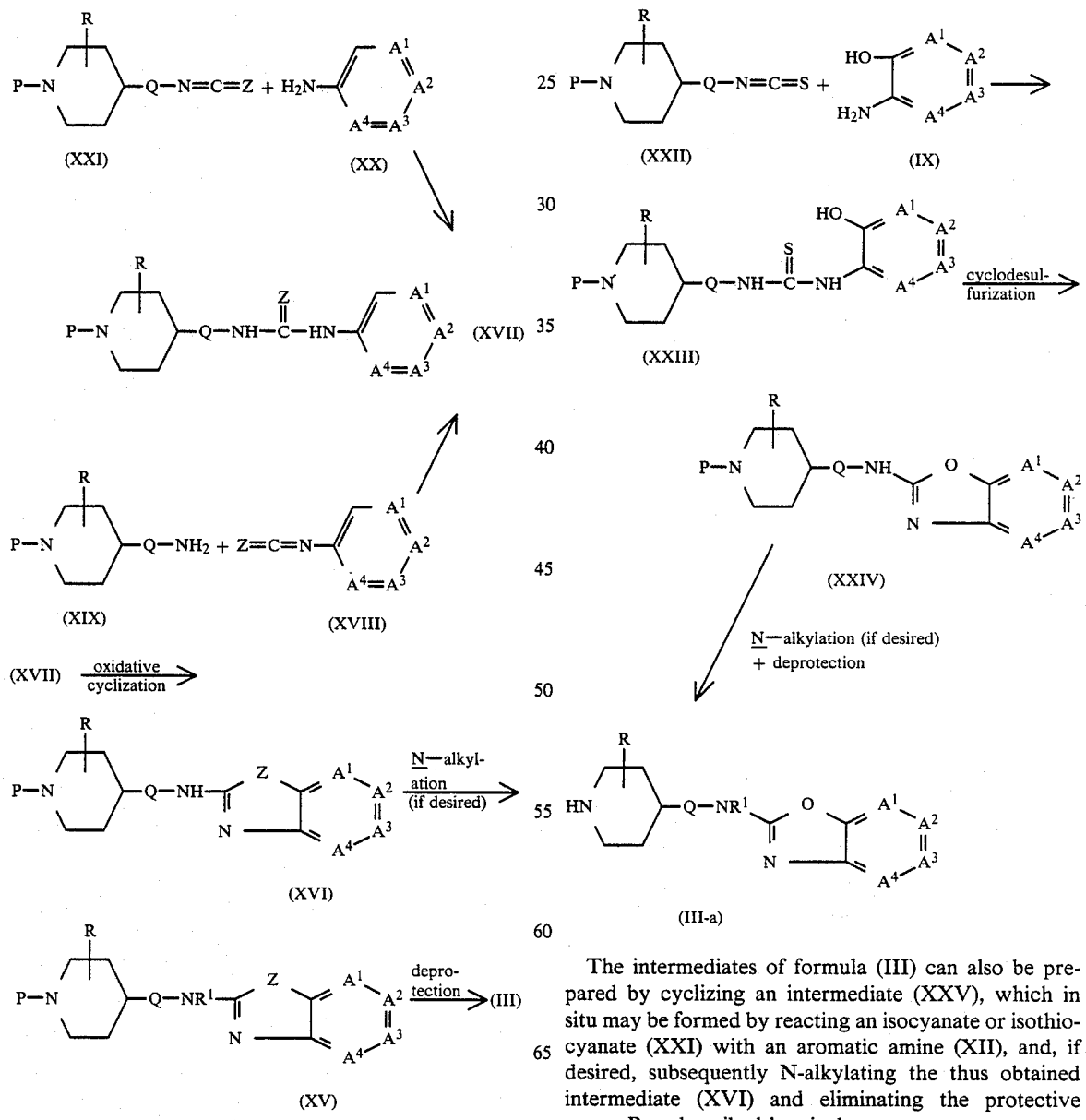

The intermediates of formula (III) can also be prepared by cyclizing an intermediate (XXV), which in situ may be formed by reacting an isocyanate or isothiocyanate (XXI) with an aromatic amine (XII), and, if desired, subsequently N-alkylating the thus obtained intermediate (XVI) and eliminating the protective group P as described hereinabove.

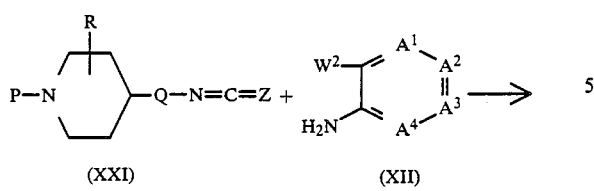

(XXI)       (XII)

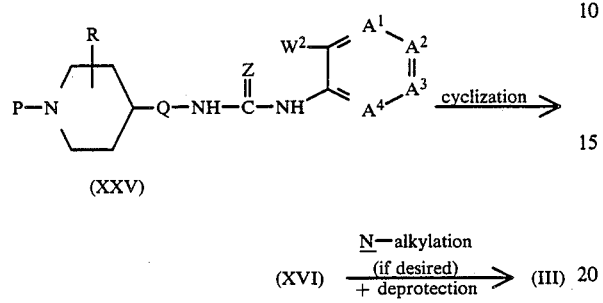

(XXV)

$$(XVI) \xrightarrow[\text{+ deprotection}]{\underline{N}\text{—alkylation (if desired)}} (III)$$

The intermediates of formula (III) may be prepared by reacting a bicyclic condensed oxazol- or thiazol of formula (VII) with a piperidine of formula (XXVI), wherein $E^1$ and $E^2$ are selected so that during the reaction a radical of $—NR^1—$ is formed, following the procedures described hereinabove for the preparation of (I) starting from (VI) and (VII), and subsequently eliminating the protective group P in the thus obtained intermediate (XV) as described hereinabove.

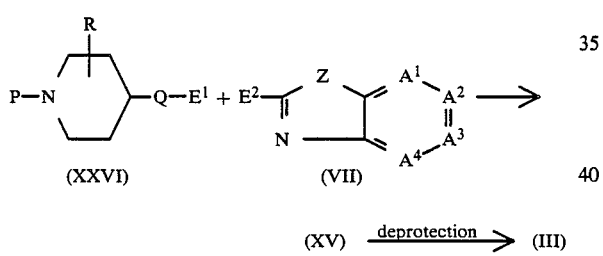

(XXVI)       (VII)

$$(XV) \xrightarrow{\text{deprotection}} (III)$$

The intermediates of formula (V) and the intermediates of formula (V) wherein $R^1$ is hydrogen, the latter intermediates being represented by the formula (V-a), can be prepared by reacting an amine (VI-a) with an aromatic isocyanate or isothiocyanate (XVIII), respectively by reacting an isocyanate or isothiocyanate (XI) with an aromatic amine (XX).

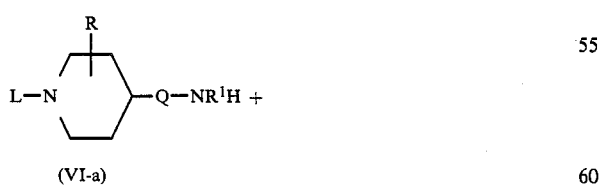

(VI-a)

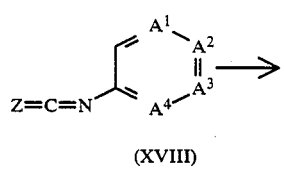

(XVIII)

-continued

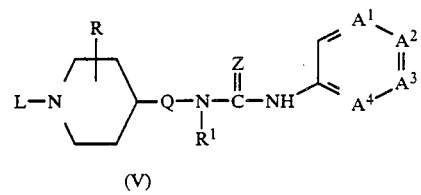

(V)

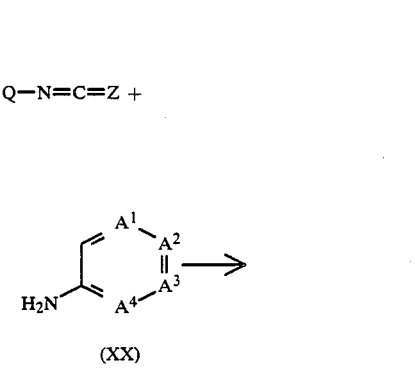

(XI)

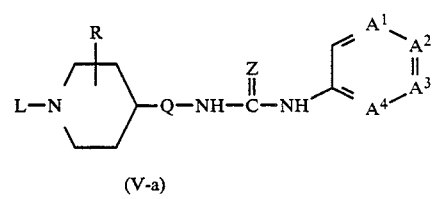

(XX)

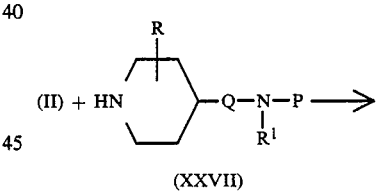

(V-a)

The intermediates of formula (VI-a) can be prepared by N-alkylating a piperidine of formula (XXVII) with a reagent of formula (II), following the above-described procedures for the preparation of (I) starting from (II) and (III), followed by the removal of P in the thus obtained intermediates (XXVIII).

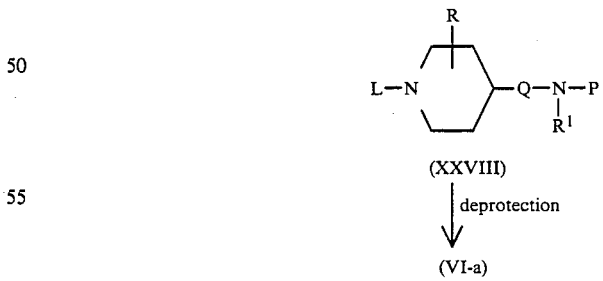

(XXVII)

(XXVIII)

↓ deprotection (VI-a)

At any stage of the above preparation schemes, the intermediates wherein $R^1$ is hydrogen may be converted into the corresponding intermediates wherein $R^1$ is other than hydrogen following art-known procedures as described hereinabove.

The compounds of formula (I) and some of the intermediates in this invention may have an asymmetric carbon atom in their structure. This chiral center may be present in a R- and a S-configuration, this R- and S-notation being in correspondence with the rules described in J. Org. Chem., 35, 2849–2867 (1970).

Pure stereochemically isomeric forms of the compounds of this invention may be obtained by the application of art-known procedures. Diastereoisomers may be separated by physical separation methods such as selective crystallization and chromatographic techniques, e.g., counter current distribution, and enantiomers may be separated from each other by the selective crystallization of their diastereomeric salts with optically active acid. They may also be derived from the corresponding pure stereochemically isomeric forms of the appropriate starting materials, provided that the reaction occurs stereospecifically.

It is evident that the cis and trans diastereomeric racemates may be further resolved into their optical isomers, cis(+), cis(−), trans(+) and trans(−) by the application of methodologies known to those skilled in the art.

Stereochemically isomeric forms of the compounds of formula (I) are naturally intended to be embraced within the scope of the invention.

The compounds of formula (I), their acid addition salts and stereochemically isomeric forms possess useful pharmacological properties. Said useful pharmacological properties can be demonstrated in, for example, the "Loss of Righting Reflex" test illustrating the xylazine antagonistic properties of the compounds of the present invention.

In view of their useful pharmacological properties, the subject compounds may be formulated into various pharmaceutical forms for administration purposes.

To prepare the pharmaceutical compositions of this invention, an effective amount of the particular compound, in base or acid-addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycol, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral doage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agent and the like may be employed. In the compositions suitable for percutaneous administration, the carrier optionally comprises a penetration enhancing agent and/or a suitable wettable agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoon-fuls and the like, and segregated multiples thereof.

As mentioned hereinabove the compounds of the present invention show xylazine-antagonistic properties. Xylazine is known in the art to produce a state of CNS depression (see, for example, Colpaert and Janssen, Eur. J. Pharmacol. 103, 169–171, 1984; Drew et al., Eur. J. Pharmacol. 42, 123–130, 1977).

In view of their capability to antagonize the effects of xylazine, the compounds of the present invention may be used as anti-depressives. Another feature of the present invention consists in the fact that the compounds of formula (I) also show anti-Parkinson properties and therefore, they may also be useful in the treatment of Parkinson's disease.

Furthermore, the compounds of formula (I), their acid addition salts or stereochemically isomeric forms also possess useful enterokinetic activity, which makes them useful in the treatment of diseases related with disturbed enterokinesia. Said usefulness enterokinetic properties can conveniently be demonstrated in a number of pharmacological tests such as, for example, in the "Enhancement of Fecal Excretion" test, whereby the fecal excretion of test animals being pre-treated with saline (controls) or with test compound is compared.

In view of the utility of the compounds of the present invention, there is provided a method of treating depressive conditions in warm blooded animals suffering from said depressive conditions. Said method comprises the administration to warm blooded animals of an anti-depressive effective amount of a compound of formula (I), a pharamceutically acceptable acid addition salt, or a stereoisomeric form thereof.

Further, there is also provided a method of treating warm blooded animals suffering from Parkinson's disease, which method comprises the systemic administration to subjects suffering from said disease of an anti-Parkinson effective amount of a compound of formula (I), a pharmaceutically acceptable acid addition salt, or a stereoisomeric form thereof.

There is furthermore provided a method of treating warm blooded animals suffering from diseases related with disturbed enterokinesia, said method comprising the systemic administration to warm blooded animals of an amount, sufficient to treat said diseases, of a compound of formula (I), a pharmaceutically acceptable acid addition salt, or a stereochemically isomeric form thereof.

Those of skill in treating depressive conditions, Parkinson's disease or diseases related with disturbed enterokinesia could easily determine the effective amount from the test results presented here. In general it is contemplated that an effective amount would be from 0.005 mg/kg to 20 mg/kg body weight, more preferably from 0.05 mg/kg to 5 mg/kg body weight.

The following examples are intended to illustrate and not to limit the present invention in all its aspects. Unless otherwise stated all parts therein are by weight.

EXAMPLES

(A)

PREPARATION OF INTERMEDIATES

EXAMPLE 1

A mixture of 64 parts of methyl 3-methyl-4-oxo-1-piperidinecarboxylate, 305 parts of nitromethane and 3.02 parts of 1,2-ethanediamine was stirred and refluxed for 4 hours. The reaction mixture was evaporated. The residue was taken up in trichloromethane. The solution was washed twice with a dilute hydrochloric acid solution, dried, filtered and evaporated, yielding 70 parts (87.2%) of methyl 3,6-dihydro-3-methyl-4-(nitromethyl)-1-(2H)-pyridinecarboxylate as a residue (intermediate 1).

In a similar manner there was also prepared:
ethyl 3,6-dihydro-4-(nitromethyl)-1(2H)-pyridinecarboxylate (intermediate 2).

EXAMPLE 2

To a stirred and cooled mixture of 85.5 parts of ethyl 4-oxo-1-piperidinecarboxylate, 33.6 parts of nitromethane and 240 parts of methanol were added dropwise 10 parts of a sodium methoxide solution 30% at 10°~15° C. Upon completion, stirring was continued first for 2 hours at about 10° C. and further overnight at room temperature. The reaction mixture was evaporated at room temperature, crushed ice was added to the oily residue and the whole was acidified with acetic acid. The product was extracted with trichloromethane. The extract was dried, filtered and evaporated. The oily residue was solidified on triturating in petroleum ether. The product was filtered off and dried, yielding 73 parts of ethyl 4-hydroxy-4-(nitromethyl)-1-piperidinecarboxylate (intermediate 3).

EXAMPLE 3

A mixture of 41 parts of ethyl 3,6-dihydro-4-(nitromethyl)-1(2H)pyridinecarboxylate and 400 parts of methanol, saturated with ammonia, was hydrogenated at normal pressure and at room temperature with 6 parts of Raney-nickel catalyst. After the calculated amount of hydrogen was taken up, the catalyst was filtered off and the filtrate was evaporated, yielding 35 parts (98.9%) of ethyl 4-(aminomethyl)-1-piperidinecarboxylate (intermediate 4).

In a similar manner there was also prepared:
methyl cis-4-(aminomethyl)-3-methyl-1-piperidinecarboxylate (intermediate 5).

EXAMPLE 4

A mixture of 73 parts of ethyl 4-hydroxy-4-(nitromethyl)-1-piperidinecarboxylate, 400 parts of methanol and 150 parts of acetic acid was hydrogenated in the Parr-apparatus with 5 parts of palladium-on-charcoal catalyst 10%. After the calculated amount of hydrogen was taken up, the catalyst was filtered off and the filtrate was evaporated. To the residue was added crushed ice and the whole was alkalized with potassium hydroxide. The aqueous phase was salted out with potassium carbonate and the product was extracted with benzene. The extract was dried, filtered and evaporated, yielding 63.5 parts of ethyl 4-(aminomethyl)-4-hydroxy-1-piperidinecarboxylate; mp. ±82° C. (intermediate 6).

In a similar manner there were also prepared:
ethyl 4-[[(phenylmethyl)amino]methyl]-1-piperidinecarboxylate (intermediate 7):
ethyl 4-[[(2-phenylethyl)(phenylmethyl)amino]methyl]-1-piperidinecarboxylate (intermediate 8); and
ethyl 4-[3-[(phenylmethyl)amino]propyl]-1-piperidinecarboxylate (intermediate 9).

EXAMPLE 5

To a stirred and cooled ($-10°$ C.) mixture of 41.6 parts of N,N'-methanetetraylbis[cyclohexanamine], 101 parts of carbon disulfide and 450 parts of tetrahydrofuran was added dropwise a solution of 31.2 parts of 1-acetyl-4-piperidinmethanamine in 90 parts of tetrahydrofuran. Upon completion, stirring was continued overnight at room temperature. The reaction mixture was evaporated, 2,2'-Oxybispropane was added to the residue. The precipitate was filtered off and the filtrate was evaporated, yielding 40 parts (100%) of 1-acetyl-4-(isothiocyanatomethyl) piperidine as a residue (intermediate 10).

In a similar manner there was also prepared:
2,3-dihydro-6-isothiocyanato-1,4-benzodioxin (intermediate 11).

EXAMPLE 6

A mixture of 4 parts of 1-acetyl-4-(isothiocyanatomethyl)piperidine, 2.2 parts of 4-fluorobenzenamine and 90 parts of tetrahydrofuran was stirred overnight at reflux temperature. The reaction mixture was evaporated, yielding 6.2 parts (100%) of N-[(1-acetyl-4-piperidinyl)methyl]-N'-(4-fluorophenyl)thiourea as a residue (intermediate 12).

In a similar manner there was also prepared:
N-[(1-acetyl-4-piperidinyl)methyl]-N'-(2-fluorophenyl)-thiourea (intermediate 13).

EXAMPLE 7

A mixture of 3.1 parts of 1-acetyl-4-piperidinemethanamine, 3.4 parts of 1-chloro-4-isothiocyanatobenzene and 90 parts of tetrahydrofuran was stirred for 3 hours at room temperature. The reaction mixture was evaporated, yielding 6.5 parts (99.7%) of N-[(1-acetyl-4-piperidinyl)methyl]-N'-(4-chlorophenyl)thiourea as a residue (intermediate 14).

In a similar manner there were also prepared:

TABLE I

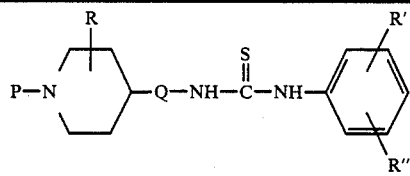

| No. | P | R | Q | R' | R'' | isomerism | mp. (°C.) |
|---|---|---|---|---|---|---|---|
| 15 | C₂H₅OCO | 4-OH | CH₂ | H | H | — | 157.8 |
| 16 | CH₃CO | H | CH₂ | H | H | — | 175.1 |
| 17 | C₂H₅OCO | H | CH₂ | H | 4-CH₃ | — | — |
| 18 | C₂H₅OCO | H | CH₂ | H | 2-Cl | — | oil |
| 19 | C₂H₅OCO | H | CH₂ | H | 2-CH₃ | — | — |
| 20 | C₂H₅OCO | H | CH₂ | H | 4-OH | — | oil |
| 21 | C₂H₅OCO | H | CH₂ | 3-CH₃O | 5-CH₃O | — | — |
| 22 | C₂H₅OCO | H | CH₂ | 2-CH₃O | 5-CH₃O | — | oil |
| 23 | CH₃CO | H | CH₂ | 2-CH₃O | 4-CH₃O | — | 157.0 |
| 24 | CH₃CO | H | CH₂ | 3-O—CH₂—O—4 | | — | — |
| 25 | CH₃CO | H | CH₂ | 3-O—C₂H₄—O—4 | | — | — |
| 26 | C₂H₅OCO | H | C₂H₄ | 3-CH₃O | 5-CH₃O | — | 134 |
| 27 | CH₃OCO | 3-CH₃ | CH₂ | H | H | cis | oil |

In a similar manner there was also prepared:
N-[(1-acetyl-4-piperidinyl)methyl]-N'-(3,4,5-trimethoxyphenyl)thiourea (intermediate 28).

EXAMPLE 8

To a stirred mixture of 5.8 parts of N-[(1-acetyl-4-piperidinyl)methyl]-N'-phenylthiourea and 160 parts of tetrachloromethane were added 3.7 parts of bromine. The whole was stirred and refluxed for 15 minutes. After the additions of 16 parts of ethanol and 16 parts of acetonitrile, the reaction mixture was cooled. The precipitated product was filtered off, washed with acetonitrile and dried. The hydrobromide salt was dissolved in methanol and water. This solution was alkalized with ammonium hydroxide. The precipitated product was filtered off, washed with water and dried, yielding 2.7 parts of 1-acetyl-N-(2-benzothiazolyl)-4-piperidinemethanamine; m.p. 138.1° C. (intermediate 29).

In a similar manner there were also prepared:

EXAMPLE 9

A mixture of 33.3 parts of N-[(1-acetyl-4-piperidinyl)methyl]-N'-(1,3-benzodioxol-5-yl)thiourea, 112.5 parts of a hydrobromic acid solution 48% in water and 75 parts of water was stirred till all solid entered the solution. Then there were added 16 parts of bromine and stirring was continued overnight at reflux. After cooling, the product was filtered off, washed with ethanol and dried, yielding 26.5 parts (58.4%) of N-(4-piperidinylmethyl)-1,3-dioxolo[4,5-f]benzothiazol-6-amine dihydrobromide; mp. >260° C. (intermediate 44).

In a similar manner there was also prepared:
6,7-dihydro-N-(4-piperidinylmethyl)-[1,4]-dioxino[2,3-f]benzothiazol-2-amine dihydrobromide; mp. 285.2° C. (intermediate 45).

EXAMPLE 10

TABLE II

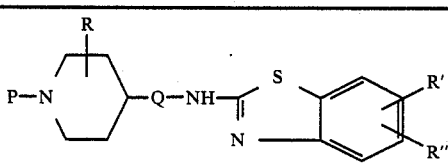

| No. | P | R | Q | R' | R'' | isomerism | salt/base | mp. (°C.) |
|---|---|---|---|---|---|---|---|---|
| 30 | C₂H₅OCO | 4-OH | CH₂ | H | H | — | base | 100 |
| 31 | CH₃CO | H | CH₂ | H | 6-Cl | — | HBr | — |
| 32 | CH₃CO | H | CH₂ | H | 6-F | — | HBr | — |
| 33 | CH₃CO | H | CH₂ | H | 4-F | — | HBr | — |
| 34 | C₂H₅OCO | H | CH₂ | H | 6-CH₃ | — | HBr | — |
| 35 | C₂H₅OCO | H | CH₂ | H | 4-Cl | — | HBr | — |
| 36 | C₂H₅OCO | H | CH₂ | H | 4-CH₃ | — | HBr | — |
| 37 | C₂H₅OCO | H | CH₂ | H | 6-OH | — | base | oil |
| 38 | C₂H₅OCO | H | CH₂ | 5-CH₃O | 7-CH₃O | — | HBr | — |
| 39 | C₂H₅OCO | H | CH₂ | 4-CH₃O | 7-CH₃O | — | base | — |
| 40 | CH₃CO | H | CH₂ | 5-CH₃O | 6-CH₃O | — | base | — |
| 41 | C₂H₅OCO | H | C₂H₄ | 5-CH₃O | 7-CH₃O | — | HBr | — |
| 42 | CH₃OCO | 3-CH₃ | CH₂ | H | H | cis | HBr | — |

In a similar manner there was also prepared:
1-acetyl-N-(5,6,7-trimethoxy-2-benzothiazolyl)-4-piperidinemethanamine (intermediate 43).

To a stirred and cooled (below 25° C.) mixture of 13.9 parts of 7-aminothiazolo[5,4-d]pyrimidin-2-thiol and 180 parts of N,N-dimethylformamide were added portionwise 4.3 parts of a sodium hydride dispersion 50% while cooling. After stirring for 1 hour, 11.5 parts of iodomethane were added dropwise at a temperature below 25° C. Upon completion, stirring was continued for 4 hours at room temperature. The reaction mixture was poured into water. The product was filtered off (the filtrate was set aside) and dried, yielding a first fraction of 5.9 parts of 2-(methylthio)thiazolo[5,4-d]pyrimidin-7-amine (intermediate 46). From the filtrate, the aqueous layer was extracted with trichloromethane. The extract was dried, filtered and evaporated. The residue was stirred in 2,2'-oxybispropane. The product was filtered off and dried, yielding fraction of 3.9 parts of 2-(methylthio)thiazolo[5,4-d]pyrimidin-7-amine (intermediate 46). Total yield: 9.8 parts (65.6%) of 2-(methylthio)thiazolo[5,4-d]pyrimidin-7-amine (intermediate 46).

During 1 hour, chlorine was bubbled through a stirred and cooled emulsion of 5 parts of 2-(methylthio)thiazolo[5,4-d]pyrimidin-7-amine in 24 parts of methanol and 70 parts of water at a temperature below 10° C. After stirring for 1 hour at the same temperature, the precipitated product was filtered off, washed with water and with 2-propanone and dried, yielding 5.35 parts (80%) of 2-(methylsulfonyl)thiazolo[5,4-d]pyrimidin-7-amine monohydrochloride (intermediate 47).

EXAMPLE 11

A mixture of 13 parts of ethyl 4-(2-aminoethyl)-1-piperidinecarboxylate, 12.2 parts of 2-chlorobenzothiazole, 15 parts of sodium carbonate, 0.2 parts of sodium iodide and 18 parts of N,N-dimethylacetamide was stirred for 2 hours at 140° C. Water was added and the product was extracted with 4-methyl-2-pentanone. The extract was dried, filtered and evaporated. The residue was converted into the hydrobromide salt in acetonitrile. The salt was filtered off and dried, yielding 11 parts (40.8%) of ethyl 4-[2-[(2-benzothiazolyl)amino]ethyl]-1-piperidinecarboxylate monohydrobromide; mp. 185.5° C. (intermediate 48).

In a similar manner there were also prepared:
ethyl 4-[[(2-benzothiazolyl)(2-phenylethyl)amino]methyl]-1-piperidinecarboxylate (intermediate 49); and
ethyl 4-[3-[(2-benzothiazolyl)amino]propyl]-1-piperidinecarboxylate (intermediate 50).

EXAMPLE 12

A mixture of 11 parts of 1-acetyl-4-piperidinemethanamine and 9 parts of 2-(methylthio)thiazolo[5,4-b]pyridine was stirred and heated for 20 hours at 140° C. The whole was purified by column chromatography over silica gel using a mixture of trichloromethane and methanol (95:5 by volume) as eluent. The pure fraction were collected and the eluent was evaporated, yielding 13.5 parts (93%) of 1-acetyl-N-(thiazolo[5,4-b]pyridin-2-yl)-4-piperidinemethanamine as a residue (intermediate 51).

EXAMPLE 13

A mixture of 8.7 parts of 1-acetyl-N-(2-benzothiazolyl)-4-piperidinemethanamine, 1.44 parts of a sodium hydride dispersion 60% and 270 parts of N,N-dimethylformamide was stirred for 1 hour at room temperature. 5.48 Parts of iodomethane were added dropwise slowly. Upon completion, stirring was continued overnight at room temperature. The reaction mixture was poured into water. The product was extracted with 4-methyl-2-pentanone. The extract was dried, filtered and evaporated in vacuo. The residue was purified by column chromatography (HPLC) over silica gel using a mixture of dichloromethane and methanol (98.75:1.25 by volume) as eluent. The second fraction was collected and the eluent was evaporated, yielding 7.6 parts (84%) of 1-acetyl-N-(2-benzothiazolyl)-N-methyl-4-piperidinemethanamine as a residue (intermediate 52).

EXAMPLE 14

A mixture of 140 parts of 1-acetyl-N-(2-benzothiazolyl)-4-piperidinemethanamine and 1500 parts of a hydrobromic acid solution 24% in water was stirred and refluxed for 5 hours. The reaction mixture was evaporated and the residue was suspended in boiling ethanol. After cooling, the product was filtered off and dried, yielding 122 parts (79%) of N-(4-piperidinylmethyl)-2-benzothiazolamine dihydrobromide. hemihydrate; mp. >300° C. (intermediate 53).

In a similar manner there were also prepared:

TABLE III

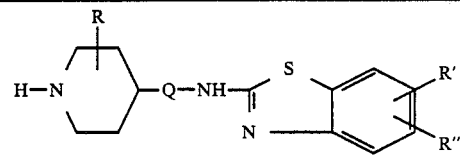

| No. | R | Q | R' | R" | isomerism | salt/base | mp. (°C.) |
|---|---|---|---|---|---|---|---|
| 54 | 4-OH | CH$_2$ | H | H | — | 2 HBr | 256.3 |
| 55 | H | CH$_2$ | H | 6-Cl | — | 2 HBr | — |
| 56 | H | CH$_2$ | H | 6-F | — | 2 HBr | — |
| 57 | H | CH$_2$ | H | 4-F | — | 2 HBr | — |
| 58 | H | CH$_2$ | H | 6-CH$_3$ | — | 2 HBr | — |
| 59 | H | CH$_2$ | H | 4-Cl | — | 2 HBr | — |
| 60 | H | CH$_2$ | H | 4-CH$_3$ | — | 2 HBr | — |
| 61 | H | CH$_2$ | H | 6-OH | — | 2 HBr | — |
| 62 | H | CH$_2$ | 5-CH$_3$O | 7-CH$_3$O | — | base | oil |
| 63 | H | CH$_2$ | 4-CH$_3$O | 7-CH$_3$O | — | 2 HBr | — |
| 64 | H | CH$_2$ | 5-CH$_3$O | 6-CH$_3$O | — | base | — |
| 65 | H | C$_2$H$_4$ | H | H | — | 2 HBr | — |
| 66 | H | C$_2$H$_4$ | 5-CH$_3$O | 7-CH$_3$O | — | 2 HBr | >260 |
| 67 | 3-CH$_3$ | CH$_2$ | H | H | cis | 2 HBr | — |
| 68 | H | C$_3$H$_6$ | H | H | — | 2 HBr | 220.1 |

In a similar manner there were also prepared:
N-(4-piperidinylmethyl)thiazolo[5,4-b]pyridin-2-amine dihydrobromide (intermediate 69):
N-methyl-N-(4-piperidinylmethyl)-2-benzothiazolamine dihydrobromide (intermediate 70);
N-(2-phenylethyl)-N-(4-piperidinylmethyl)-2-benzothiazolamine (intermediate 71);
5,6,7-trimethoxy-N-(4-piperidinylmethyl)-2-benzothiazolamine (intermediate 72).

EXAMPLE 15

A mixture of 15 parts of 4-(isothiocyanatomethyl)pyridine, 9.5 parts of 2-aminophenol and 160 parts of acetonitrile was stirred for 3 hours at room temperature. The precipitated product was filtered off, washed with 2,2'-oxybispropane and crystallized from acetonitrile, yielding 8.22 parts of N-(2-hydroxyphenyl)-N'-(4-pyridinylmethyl)thiourea; mp. 179.6° C. (intermediate 73).

A mixture of 14 parts of N-(2-hydroxyphenyl)-N'-(4-pyridinylmethyl)thiourea, 20 parts of mercury(II) oxide, 1 part of sulfur, 160 parts of 2-propanol and 160 parts of acetonitrile was stirred and refluxed for 14 hours. The reaction mixture was filtered over diatomaceous earth and the filtrate was evaporated. The oily residue was crystallized from aceonitrile, yielding 6.8 parts (56%) of N-(4-pyridinylmethyl)-2-benzoxazolamine; mp. 147.9° C. (intermediate 74).

A mixture of 4.5 parts of N-(4-pyridinylmethyl)-2-benzoxazolamine and 120 parts of methanol was hydrogenated at normal pressure at about 50° C. with 2 parts of rhodium-on-charcoal catalyst 5%. After the calculated amount of hydrogen was taken up, the catalyst was filtered off and the filtrate was evaporated, yielding 4.6 parts of N-(4-piperidinylmethyl)-2-benzoxazolamine as an oily residue (intermediate 75).

EXAMPLE 16

A mixture of 3 parts of 1-(4-fluoro-2-hydroxyphenyl)ethanone, 14.9 parts of (chloromethyl)benzene, 16.4 parts of potassium carbonate, 0.1 parts of potassium iodide and 120 parts of 2-propanone was stirred overnight at reflux temperature. The reaction mixture was evaporated. The reaction mixture was poured into water. The product was extracted three times with trichloromethane. The combined extracts were dried, filtered and evaporated. The residue was crystallized from a mixture of 2-propanol and water. The product was filtered off and dried, yielding 11 parts (58%) of 1-[4-fluoro-2-(phenylmethoxy)phenyl]ethanone (intermediate 76).

A mixture of 11 parts of 1-[4-fluoro-2-(phenylmethoxy)phenyl]ethanone, 8.48 parts of 3-chlorobenzenecarboperoxoic acid and 260 parts of dichloromethane was stirred for 5 days at room temperature. The precipitate was filtered off and the filtrate was stirred in a saturate thiosulfate solution for 15 minutes. The organic layer was separated and stirred in a saturate hydrogen carbonate solution for 15 minutes. The organic layer was separated, washed with water, dried, filtered and evaporated. The solid residue was stirred in 240 parts of methanol. 5.3 Parts of sodium methoxide were added portionwise. After complete addition, the whole was stirred for 1 hour at room temperature. After evaporation in vacuo at 50° C., the residue was stirred in water and acidified with a hydrochloric acid solution 3N. Trichloromethane was added, the organic layer was separated, washed twice with water, dried, filtered and evaporated, yielding 10 parts (93%) of 4-fluoro-2-(phenylmethoxy)phenol as a residue (intermediate 77).

To a stirred mixture of 2.5 parts of 4-fluoro-2-(phenylmethoxy)phenol, 2.3 parts of 1-bromo-3-chloropropane, 10 parts of water and 0.39 parts of tetrabutylammonium hydrogen sulfate was added dropwise a solution of 0.7 parts of sodium hydroxide in 5 parts of D at 60° C. (exothermic reaction: temperature rose to 70°). The whole was stirred for 2 hours at 70° C. After cooling, the product was extracted twice with methylbenzene. The combined extracts were dried, filtered and evaporated, yielding 3.4 parts (100%) of 1-(3-chloropropoxy)-4-fluoro-2-(phenylmethoxy)benzene as a residue (intermediate 78).

EXAMPLE 17

To a stirred and cooled (0° C.) solution of 32.8 parts of 3,4-dihydro-2H-1-benzopyran-2-methanol in 70 parts of pyridine and 117 parts of benzene was added dropwise a solution of 41.9 parts of 4-methylbenzenesulfonyl chloride in 63 parts of benzene. Upon completion, stirring was continued for 25 hours. The reaction mixture was washed successively with a hydrochloric acid solution 10%, with water and with a sodium carbonate solution 10%. The organic layer was dried, filtered and evaporated. The residue was purified by column chromatography over silica gel using trichloromethane as eluent. The pure fractions were collected and the eluent was evaporated, yielding
28.3 parts of 3,4-dihydro-2H-1-benzopyran-2-methanol 4-methylbenzenesulfonate(ester) as a solid residue; mp. 59.4° C. (intermediate 79).
(−)-3,4-dihydro-2H-1-benzopyran-2-methanol 4-methylbenzenesulfonate (ester) (intermediate 80); and
(+)-3,4-dihydro-2H-1-benzopyran-2-methanol 4-methylbenzenesulfonate (ester) (intermediate 81).

EXAMPLE 18

A mixture of 5 parts of 1-[(2,3-dihydro-1,4-benzodioxin-2-yl)methyl]-4-piperidinemethanamine dihydrobromide, 1.6 parts of 4-fluorobenzaldehyde, 3 parts of a solution of thiophene in methanol 4%, 200 parts of methanol and 4 parts of calcium oxide was hydrogenated at normal pressure and at room temperature with 2 parts of palladium-on-charcoal catalyst 10%. After the calculated amount of hydrogen was taken up, the catalyst as filtered off and the filtrate was evaporated, yielding 4.3 parts (98.3%) of 1-[(2,3-dihydro-1,4-benzodioxin-2-yl)methyl]-N-[(4-fluorophenyl)methyl]-4-piperidinemethanamine as an oily residue (intermediate 82).

EXAMPLE 19

A mixture of 13.2 parts of 1-[(2,3-dihydro-1,4-benzodioxin-2-yl)methyl]-α-methyl-N-(phenylmethyl)-4-piperidinemethanamine and 160 parts of methanol was hydrogenated at normal pressure and at 50° C. with 2 parts of palladium-on-charcoal catalyst 10%. After the calculated amount of hydrogen was taken up, the catalyst was filtered off and the filtrate was evaporated, yielding 8 parts (80.4%) of 1-[(2,3-dihydro-1,4-benzodioxin-2-yl)methyl]-α-methyl-4-piperidinemethanamine as an oily residue (intermediate 83).

In a similar manner there were also prepared:
ethyl 4-[[(2-phenylethyl)amino]methyl]-1-piperidinecarboxylate (intermediate 84); and
ethyl 4-(3-aminopropyl)-1-piperidinecarboxylate (intermediate 85).

EXAMPLE 20

A mixture of 22.5 parts of 2,3-dihydro-1,4-benzodioxin-2-methanol 4-methylbenzenesulfonate (ester), 11.1 parts 4-(2-methyl-1,3-dioxolan-2-yl)piperidine, 15 parts of sodium carbonate and 135 parts of N,N-dimethylacetamide was stirred overnight at 75° C. Water was added. The product was extracted with 4-methyl-2-pentanone. The extract was dried, filtered and evaporated, yielding 20.6 parts (100%) of 1-[(2,3-dihydro-1,4-benzodioxin-2-yl)methyl]-4-(2-methyl-1,3-dioxolan-2-yl)piperidine as an oily residue (intermediate 86).

A mixture of 20.6 parts of 1-[(2,3-dihydro-1,4-benzodioxin-2-yl)methyl]-4-(2-methyl-1,3-dioxolan-2-yl)piperidine and 200 parts of a hydrochloric acid solution 2N was stirred and refluxed for 15 hours. After cooling, crushed ice was added. The whole was treated with a sodium hydroxide solution. The product was extracted with dichloromethane. The extract was dried, filtered and evaporated. The residue was purified by column chromatography over silica gel using a mixture of trichloromethane and methanol (99:1 by volume) as eluent. The pure fractions were collected and the eluent was evaporated, yielding 10 parts (55.8%) of 1-[1-[(2,3- dihydro-1,4-benzodioxin-2-yl)methyl]-4-piperidinyl]ethanone as an oily residue (intermediate 87).

A mixture of 10 parts of 1-[1-[(2,3-dihydro-1,4-benzodioxin-2-yl)methyl]-4-piperidinyl]ethanone, 3.8 parts of benzenemethanamine, 1 part of a solution of thiophene in methanol 4% and 160 parts of methanol was hydrogenated at normal pressure and at 50° C. with 2 parts of palladium-on-charcoal catalyst 10%. After the calculated amount of hydrogen was taken up, the catalyst was filtered off and the filtrate was evaporated, yielding 13.2 parts (100%) of 1-[(2,3-dihydro-1,4-benzodioxin-2-yl)methyl]-α-methyl-N-(phenylmethyl)-4-piperidinemethanamine as an oily residue (intermediate 88).

EXAMPLE 21

A mixture of 12.6 parts of 2-(bromomethyl)-2,3-dihydro-1,4-benzodioxin, 11 parts of N-(4-piperidinylmethyl)acetamide acetate (1:1), 15 parts of sodium carbonate, 0.1 parts of sodium iodide and 135 parts of N,N-dimethylacetamide was stirred overnight at 75° C. The reaction mixture was poured into water. The product was extracted with 4-methyl-2-pentanone. The extract was dried, filtered and evaporated. The residue was crystallized from a mixture of 1,1'-oxybisethane and 2,2'-oxybispropane. The product was filtered off and dried, yielding 3.2 parts (21.0%) of N-[[1-[(2,3-dihydro-1,4-benzodioxin-2-yl)methyl]-4-piperidinyl]methyl]acetamide; mp. 137.9° C. (intermediate 89).

A mixture of 2 parts of N-[[1-[(2,3-dihydro-1,4-benzodioxin-2-yl)methyl]-4-piperidinyl]methyl]acetamide, 15 parts of a hydrobromic acid solution 48% in water and 10 parts of water was stirred for 4 hours at reflux temperature. The reaction mixture was evaporated. The residue was crystallized from a mixture of ethanol and acetonitrile. The product was filtered off and dried, yielding 2 parts of 1-[(2,3-dihydro-1,4-benzodioxin-2-yl)methyl]-4-piperidinemethanamine dihydrobromide; mp. 235.3° C. (intermediate 90).

A mixture of 6.4 parts of (1-[(2,3-dihydro-1,4-benzodioxin-2-yl)methyl]-4-piperidinemethanamine dihydrobromide, 4 parts of calcium oxide and 80 parts of methanol was stirred for 3 hours at room temperature. Then there were added 5 parts of 1-isothiocyanato-4-methoxybenzene and the whole was stirred for 3 hours at room temperature. The whole was filtered and the filtrate was evaporated. The sticky residue was suspended in a mixture of 1,1'-oxybisethane and 2,2'-oxybispropane, the latter was decanted (the residue was set aside) and allowed to crystallize, yielding a first fraction of 1 part of N-[[1-[(2,3-dihydro-1,4-benzodioxin-2-yl)methyl]-4-piperidinyl]methyl]-N'-(4-methoxyphenyl)thiourea (intermediate 91). The residue, which was set aside, yield a second fraction of 5 parts of N-[[1-[(2,3-dihydro-1,4-benzodioxin-2-yl)methyl]-4-piperidinyl]methyl]-N'-(4-methoxyphenyl)thiourea (intermediate 91). Total yield: 6 parts (93.5%) of N-[[1-[(2,3-dihydro-1,4-benzodioxin-2-yl)methyl]-4-piperidinyl]methyl]-N'-(4-methoxyphenyl)thiourea; mp. 147.9° C. (intermediate 91).

(B)

PREPARATION OF FINAL COMPOUNDS

EXAMPLE 22

A mixture of 3.8 parts of 2-(bromomethyl)-2,3-dihydro-1,4-benzodioxin, 6.3 parts of N-(4-piperidinylmethyl)-2-benzothiazolamine dihydrobromide, 10 parts of sodium carbonate, 0.1 parts of sodium iodide and 68 parts of N,N-dimethylformamide was stirred for 48 hours at 70° C. The reaction mixture was poured into water and the product was extracted with 4-methyl-2-pentanone. The extract was dried, filtered and evaporated. The oily residue was crystallized from acetonitrile, yielding 2.8 parts of N-[[1-[(2,3-dihydro-1,4-benzodioxin-2-yl)methyl]-4-piperidinyl]methyl]-2-benzothiazolamine; mp. 139.9° C. (compound 1).

In a similar manner there were also prepared:
4-(2-benzothiazolylaminomethyl)-1-(2-phenoxyethyl)-4-piperidinol dihydrochloride; mp. 209.3° C. (compound 2);

N-[1-(2-phenoxyethyl)-4-piperidinylmethyl]-2-benzothiazolamine; mp. 116.1° C. (compound 3);

N-[1-(3-phenoxypropyl)-4-piperidinylmethyl]-2-benzothiazolamine; mp. 113.7° C. (compound 4); and 4-(2-benzothiazolylaminomethyl)-1-(2,3-dihydro-1,4-benzodioxin-2-yl-methyl)-4-piperidinol; mp. 176.2° C. (compound 5).

EXAMPLE 23

A mixture of 2.7 parts of (R)-(−)-2,3-dihydro-1,4-benzodioxin-2-methanol 4-methylbenzenesulfonate(ester), 3.2 parts of N-(4-piperidinylmethyl)-2-benzothiazolamine dihydrobromide hemihydrate, 2.5 parts of sodium carbonate and 76.5 parts of N,N-dimethylformamide was stirred overnight at 70° C. After cooling, the reaction mixture was poured into water. The product was extracted three times with 4-methyl-2-pentanone. The combined extracts were dried, filtered and evaporated. The residue was purified by reversed phase chromatography (HPLC) over Li Chroprep RP 18 using a mixture of trichloromethane, hexane and methanol (10:10:1 by volume) as eluent. The pure fractions were collected and the eluent was evaporated. The residue was crystallized from acetonitrile. The product was filtered off and dried, yielding 1.3 parts (38.6%) of (S)-(−)-N-[[1-[(2,3-dihydro-1,4-benzodioxin-2-yl)methyl]-4-piperidinyl]methyl]-2-benzothiazolamine; mp. 133.3° C.: $[\alpha]_{589} = -15.8698°$ (c=0.5% in trichloromethane) (compound 6).

In a similar manner there were also prepared:
(R)-(+)-N-[[1-[(2,3-dihydro-1,4-benzodioxin-2-yl)methyl]-4-piperidinyl]methyl]-2-benzothiazolamine; mp. 133.1° C.: $[\alpha]_{589} = +16.6497°$ (c=0.5% in trichloromethane) (compound 7);

N-[[1-[(2,3-dihydro-1,4-benzodioxin-2-yl)methyl]-4-piperidinyl]methyl]thiazolo[5,4-b]pyridin-2-amine; mp. 158.4° C. (compound 8);

(+)-N-[[1-[(3,4-dihydro-2H-1-benzopyran-2-yl)methyl]-4-piperidinyl]methyl]-2-benzothiazolamine; mp. 144.3° C.: $[\alpha]_{589} = +68.93°$ (c=1% in methanol) (compound 9);

(+)-(R)-N-[[1-[(2,3-dihydro-1,4-benzodioxin-2-yl)methyl]-4-piperidinyl]methyl]-N-methyl-2-benzothiazolamine; mp. 111.7° C., $[\alpha]_D = +17.07°$ (c=0.5% in trichloromethane) (compound 10);

(−)-(S)-N-[[1-[(2,3-dihydro-1,4-benzodioxin-2-yl)methyl]-4-piperidinyl]methyl]-N-methyl-2-benzothiazolamine; mp. 103.5° C., $[\alpha]_D = -15.81°$ (c=0.5% in trichloromethane) (compound 11);

(+)-(R)-N-[[1-[(2,3-dihydro-1,4-benzodioxin-2-yl)methyl-4-piperidinyl]methyl]thiazolo[5,4-b]pyridin-2-amine; mp. 159.6° C.; $[\alpha]_D = +17.00°$ (c=0.5% in trichloromethane) (compound 12);

(−)-(S)-N-[[1-[(2,3-dihydro-1,4-benzodioxin-2-yl)methyl]-4-piperidinyl]methyl]thiazolo[5,4-b]pyridin-2- amine; mp. 160.5° C.; [α]$_D$=−17.48° (c=0.5% in trichloromethane) (compound 13);

(−)-N-[[1-[(3,4-dihydro-2H-1-benzopyran-2-yl)methyl]-4-piperidinyl]methyl]thiazolo[5,4-b]pyridin-2-amine; mp. 177.4° C., [α]=−49.44° (c=1% in trichloromethane) (compound 14); and N-[[1-[(2,3-dihydro-1,4-benzodioxin-2-yl)methyl]-4-piperidinyl]methyl]5,7-dimethoxy-2-benzothiazolamine; mp. 165.8° C. (compound 15).

EXAMPLE 24

A mixture of 1.9 parts of 2-(bromomethyl)-2,3-dihydro-1,4-benzodioxin, 3.3 parts of 6-chloro-N-(4-piperidinylmethyl)-2-benzothiazolamine dihydrobromide, 5 parts of sodium carbonate, 0.1 parts of sodium iodide and 67.5 parts of N,N-dimethylacetamide was stirred overnight at about 75° C. Water was added to the reaction mixture and the product was extracted with 4-methyl-2-pentanone. The extract was dried, filtered and evaporated. The oily residue was crystallized from a mixture of 1,1′-oxybisethane and 2,2′-oxybispropane. The product was filtered off and dried, yielding 1.8 parts (59.8%) of 6-chloro-N-[[1-[(2,3-dihydro-1,4-benzodioxin-2-yl)methyl]-4-piperidinyl]-methyl]-2-benzothiazolamine; mp. 155.8° C. (compound 16).

In a similar manner there were also prepared:
N-[[1-[2-(2,6-dichlorophenoxy)ethyl]-4-piperidinyl]methyl]-2-benzothiazolamine dihydrobromide; mp. 222.3° C. (compound 17);

N-[[1-[2-(2,6-dimethoxyphenoxy)ethyl]-4-piperidinyl]methyl]-2-benzothiazolamine dihydrobromide; mp. 171.3° C. (compound 18);

N-[[1-[(2,3-dihydro-1,4-benzodioxin-2-yl)methyl]-4-piperidinyl]methyl]6-fluoro-2-benzothiazolamine; mp. 152.0° C. (compound 19);

N-[[1-[(2,3-dihydro-1,4-benzodioxin-2-yl)methyl]-4-piperidinyl]methyl]4-fluoro-2-benzothiazolamine; mp. 159.8° C. (compound 20);

N-[[1-[(2,3-dihydro-1,4-benzodioxin-2-yl)methyl]-4-piperidinyl]methyl]-6-methyl-2-benzothiazolamine; mp. 123.6° C. (compound 21);

4-chloro-N-[[1-[(2,3-dihydro-1,4-benzodioxin-2-yl)methyl]-4-piperidinyl]methyl]-2-benzothiazolamine dihydrobromide; mp. 249.8° C. (compound 22); and N-[[1-[(2,3-dihydro-1,4-benzodioxin-2-yl)methyl]-4-piperidinyl]methyl]-4-methyl-2-benzothiazolamine dihydrobromide; mp. 246.4° C. (compound 23).

EXAMPLE 25

A mixture of 3.2 parts of 1-(3-chloropropoxy)-4-fluoro-2-(phenylmethoxy)benzene, 4.1 parts of N-(4-piperidinylmethyl)-2-benzothiazolamine dihydrobromide, 6 parts sodium carbonate, 0.1 parts of sodium iodide and 67.5 parts of N,N-dimethylacetamide was stirred overnight at 75° C. Water was added and the product was extracted with 4-methyl-2-pentanone. The extract was dried, filtered and evaporated. The oily residue was crystallized from acetonitrile. The product was filtered off and dried, yielding 3.3 parts (65.2%) of N-[[1-[3-[4-fluoro-2-(phenylmethoxy)phenoxy]propyl]-4-piperidinyl]methyl]-2-benzothiazolamine; mp. 129.5° C. (compound 24).

In a similar manner there was also prepared:
N-[[1-[3-(4-fluorophenoxy)propyl]-4-piperidinyl]methyl]-2-benzothiazolamine dihydrobromide.hemihydrate; mp. 172.0° C. (compound 25).

EXAMPLE 26

A mixture of 2.8 parts of 2,3-dihydro-1,4-benzodioxin-2-methanol methanesulfonate (ester), 3.4 parts of 5,6,7-trimethoxy-N-(4-piperidinylmethyl)-2-benzothiazolamine, 3 parts of sodium carbonate and 67.5 parts of N,N-dimethylacetamide was stirred overnight at about 75° C. Water was added. The product was extracted with 4-methyl-2-pentanone. The extract was dried, filtered and evaporated. The residue was purified by column chromatography over silica gel using a mixture of trichloromethane and methanol (97:3 by volume) as eluent. The pure fractions were collected and the eluent was evaporated. The residue was converted into the (E)-2-butenedioate salt in ethanol and 2-propanone. The salt was filtered off and dried, yielding 3.2 parts (48.5%) of N-[[1-[(2,3-dihydro-1,4-benzodioxin-2-yl)methyl]-4-piperidinyl]methyl]-5,6,7-trimethoxy-2-benzothiazolamine (E)-2-butenedioate (2:3); mp. 171.6° C. (compound 26).

. In a similar manner there were also prepared:
N-[[1-[(2,3-dihydro-1,4-benzodioxin-2-yl)methyl]-4-piperidinyl]methyl]5,6-dimethoxy-2-benzothiazolamine; mp. 152.8° C. (compound 27);

N-[[1-[(2,3-dihydro-1,4-benzodioxin-2-yl)methyl]-4-piperidinyl]methyl]1,3-dioxolo[4,5-f]benzothiazol-6-amine; mp. 160.1° C. (compound 28);

N-[[1-[(2,3-dihydro-1,4-benzodioxin-2-yl)methyl]-4-piperidinyl]methyl]6,7-dihydro-[1,4]-dioxino-[2,3-f]benzothiazol-2-amine; mp. 137.4° C. (compound 29); and N-[2-[1-[(2,3-dihydro-1,4-benzodioxin-2-yl)methyl]-4-piperidinyl]ethyl]2-benzothiazolamine; mp. 121.7° C. (compound 30).

EXAMPLE 27

A mixture of 3.5 parts of 3,4-dihydro-2H-1-benzopyran-2-methanol 4-methylbenzenesulfonate(ester), 4.7 parts of 6,7-dihydro-N-(4-piperidinylmethyl)-[1,4]-dioxino[2,3-f]benzothiazol-2-amine dihydrobromide, 6 parts of sodium carbonate and 67.5 parts of N,N-dimethylacetamide was stirred overnight at 70° C. On the addition of water, the product was extracted with 4-methyl-2-pentanone. The extract was dried, filtered and evaporated. The residue was converted into the hydrobromide salt in 2-propanone. The salt was filtered off and dried, yielding 4.5 parts (71.3%) of N-[[1-[(3,4-dihydro-2H-1-benzopyran-2-yl)methyl]-4-piperidinyl]methyl]-6,7-dihydro-[1,4]-dioxino[2,3-f]benzothiazol-2-amine dihydrobromide; mp.>260° C. (compound 31).

In a similar manner there were also prepared:

TABLE IV

| No. | X | R | Q | R' | R" | isomeric form | [α]* | salt/base | mp. (°C.) |
|-----|---|---|---|----|----|---------------|------|-----------|-----------|
| 32 | O | H | $CH_2$ | 4-$CH_3O$ | 7-$CH_3O$ | — | — | base | 184.4 |
| 33 | O | H | $CH_2$ | 5-$CH_3O$ | 7-$CH_3O$ | (+)-(R) | +15.27 | base | 167.1 |
| 34 | O | H | $CH_2$ | 5-$CH_3O$ | 7-$CH_3O$ | (−)-(S) | −17.88 | base | 166.6 |
| 35 | $CH_2$ | H | $CH_2$ | 5-$CH_3O$ | 6-$CH_3O$ | — | — | base | 92.9 |
| 36 | $CH_2$ | H | $CH_2$ | 5-$CH_3O$ | 7-$CH_3O$ | — | — | 2 HCl | 228.1 |
| 37 | $CH_2$ | H | $C_2H_4$ | 5-$CH_3O$ | 7-$CH_3O$ | — | — | 2 HBr | 247.7 |
| 38 | $CH_2$ | 3-$CH_3$ | $CH_2$ | H | H | cis | — | 2 HBr | 265.3 |
| 39 | $CH_2$ | H | $CH_2$ | 5-O—$CH_2$—O—6 | | — | — | 2 HBr | 275.1 |
| 40 | $CH_2$ | H | $C_3H_6$ | H | H | — | — | base | 104.2 |

*c = 0.5% in dichloromethane

In a similar manner there were also prepared:
N-[[1-[(2,3-dihydro-1,4-benzodioxin-2-yl)methyl]-4-piperidinyl]methyl]-N-(2-phenylethyl)-2-benzothiazolamine (E)-2-butenedioate(1:1); mp. 174.8° C. (compound 41);

N-[8 1-[(2,3-dihydro-1,4-benzodioxin-2-yl)methyl]-4-piperidinyl]methyl]-2-benzoxazolamine dihydrochloride; mp. 231.6° C. (compound 42);

N-[[1-[2-(4-fluorophenoxy)ethyl]-4-piperidinyl]methyl]-2-benzothiazolamine; mp. 116.8° C. (compound 43);

N-[[1-[2-(4-fluorophenoxy)ethyl]-4-piperidinyl]methyl]-5,6-dimethoxy-2-benzothiazolamine; mp. 139.7° C. (compound 44);

N-[[1-[2-(4-fluorophenoxy)ethyl]-4-piperidinyl]methyl]-5,6,7-trimethoxy-2-benzothiazolamine dihydrobromide; mp. 220.9° C. (compound 45);

(−)-(S)-N-[[1-[(2,3-dihydro-1,4-benzodioxin-2-yl)methyl]-4-piperidinyl]methyl]-5,6,7-trimethoxy-2-benzothiazolamine dihydrochloride; mp. 215.4° C., $[α]_D^{25}$ = −42.73 (c=0.5% methanol) (compound 46);

(+)-(R)-N-[[1-(2,3-dihydro-1,4-benzodioxin-2-yl)methyl]-4-piperidinyl]methyl]-5,6,7-trimethoxy-2-benzothiazolamine dihydrochloride; mp. 217.2° C., $[α]_D^{25}$ = +42.77 (c=0.5% methanol) (compound 47);

N-[[1-[2-(2-methoxyphenoxy)ethyl]-4-piperidinyl]methyl]-2-benzothiazolamine; mp. 121.1° C. (compound 48);

N-[[1-[2-(2-methylphenoxy)ethyl]-4-piperidinyl]methyl]-2-benzothiazolamine; mp. 126.4° C. (compound 49);

N-[2-[1-[2-(4-fluorophenoxy)ethyl]-4-piperidinyl]ethyl]-5,7-dimethoxy-2-benzothiazolamine; mp. 131.8° C. (compound 50);

N-[[1-[2-(4-fluorophenoxy)ethyl]-4-piperidinyl]methyl]-5,7-dimethoxy-2-benzothiazolamine dihydrobromide; mp. 249.2° C. (compound 51); and cis-N-[[1-[2-(4-fluorophenoxy)ethyl]-3-methyl-4-piperidinyl]methyl]-2-benzothiazolamine; mp. 95.9° C. (compound 52).

In a similar manner there is also prepared: N-[3-[1-(2,3-dihydro-1,4-benzodioxin-2-yl)methyl]-4-piperidinyl]propyl]-5,6-dimethoxy-2-benzothiazolamine (compound 53).

EXAMPLE 28

A mixture of 3.2 parts of 3,4-dihydro-2H-1-benzopyran-2-methyl 4-methylbenzenesulfonate(ester), 4.2 parts of N-(4-piperidinylmethyl)-2-benzothiazolamine dihydrobromide hemihydrate, 5.3 parts of sodium carbonate, 240 parts of 4-methyl-2-pentanone was stirred and refluxed for 24 hours using a water-separator. The reaction mixture was cooled, washed with water, dried, filtered and evaporated. The residue was purified by column chromatography over silica gel using a mixture of trichloromethane and methanol (93:7 by volume) as eluent. The pure fractions were collected and the eluent was evaporated. The residue was crystallized from 2,2'-oxybispropane. The product was filtered off and dried, yielding 1.92 parts (48.8%) of N-[[1-[3,4-dihydro-2H-1-benzopyran-2-yl)methyl]-4-piperidinyl]methyl]-2-benzothiazolamine; m.p. 150.0° C. (compound 54).

In a similar manner there were also prepared:
(±)-N-[[1-[(2,3-dihydro-2-methyl-1,4-benzodioxin-2-yl)methyl]-4-piperidinyl]methyl]-2-benzothiazolamine; mp. 126.2° C. (compound 55); and (−)-N-[[1-[(3,4-dihydro-2H-1-benzopyran-2-yl)methyl]-4-piperidinyl]methyl]-2-benzothiazolamine; mp. 145.1° C. (compound 56).

EXAMPLE 29

A mixture of 4.2 parts of 2,3-dihydro-1,4-benzodioxin-2-methanol 4-methylbenzenesulfonate(ester), 5.1 parts of 2-[(4-piperidinylmethyl)amino]-6-benzothiazolol dihydrobromide, 10.5 parts of N,N-diethylethanamine and 67.5 parts of N,N-dimethylacetamide was stirred overnight at 80° C. Water was added. The product was extracted with 4-methyl-2-pentanone. The extract was dried, filtered and evaporated. The residue was converted into the hydrochloride salt in 2-propanol. The whole was evaporated. The oily residue was crystallized from a mixture of ethanol and acetonitrile. The product was filtered off and dried, yielding 2.2 parts (36.4%) of 2-[[[1-[(2,3-dihydro-1,4-benzodioxin-2-yl)methyl]-4-piperidinyl]methyl]amino]-6-benzothiazolol dihydrochloride; mp. 218.6° C. (compound 57).

EXAMPLE 30

A mixture of 6.7 parts of 1-[(2,3-dihydro-1,4-benzodioxin-2-yl)methyl]-4-piperidinemethanamine dihydrobromide, 3.26 parts of 2-(methylsulfonyl)thiazolo[4,5-c]pyridine, 4.25 parts of sodium carbonate and 18 parts of N,N-dimethylacetamide was stirred for 2 hours at 150° C. The reaction mixture was poured into ice water. The product was extracted with 4-methyl-2-pentanone. The extract was dried, filtered and evaporated. The residue was purified by column chromatography over silica gel using a mixture of trichloromethane and methanol (97:3 by volume) as eluent. The pure fractions were collected and the eluent was evaporated. The residue was crystallized from 1,1'-oxybisethane. The product was filtered off and dried, yielding 1.15 parts (20%) of N-[[1-[(2,3-dihydro-1,4-benzodioxin-2-yl)methyl]-4-piperidinyl]methyl]thiazolo[4,5-c]pyridin-2-amine; mp. 147.1° C. (compound 58).

In a similar manner there was also prepared:
N-[[1-[(2,3-dihydro-1,4-benzodioxin-2-yl)methyl]-4-piperidinyl]methyl]thiazolo[5,4-d]pyrimidine-2,7-diamine; mp. 188.8° C. (compound 59).

EXAMPLE 31

A mixture of 4 parts of 1-[(2,3-dihydro-1,4-benzodioxin-2yl)methyl]-α-methyl-4-piperidinemethanamine, 2.7 parts of 2-chlorobenzothiazole, 1.5 parts of calcium oxide and 18 parts of N,N-dimethylacetamide was stirred for 4 hours at 140° C. The whole was filtered and to the filtrate was added 4-methyl-2-pentanone. The whole was washed with water, dried, filtered and evaporated. The residue was purified by column chromatography over silica gel using a mixture of trichloromethane and methanol (97:3 by volume) as eluent. The pure fractions were collected and the eluent was evaporated. The residue was converted into the ethanedioate salt in ethanol and acetonitrile. The salt was filtered off and dried, yielding 3.4 parts (39.7%) of N-[1-[1-[(2,3-dihydro-1,4-benzodioxin-2-yl)methyl]-4-piperidinyl]ethyl]-2-benzothiazolamine ethanedioate(1:2); mp. 179.6° C. (compound 60).

In a similar manner there was also prepared:
N-[[1-[(2,3-dihydro-1,4-benzodioxin-2-yl)methyl]-4-piperidinyl]methyl]-N-[(4-fluorophenyl)methyl]-2-benzothiazolamine ethanedioate(1:1); mp. 135.5° C. (compound 61).

EXAMPLE 32

To a stirred solution of 11.85 parts of N-[1-[(2,3-dihydro-1,4-benzodioxin-2-yl)methyl]-4-piperidinylmethyl]-2-benzothiazolamine in 72 parts of N,N-dimethylformamide were added portionwise 1.5 parts of a sodium hydride dispersion 50%. Upon completion, stirring was continued for 30 minutes. A solution of 4.6 parts of iodomethane in 18 parts of N,N-dimethylformamide was added dropwise. The whole was stirred overnight at room temperature. The reaction mixture was poured into water and the product was extracted twice with 4-methyl-2-pentanone. The combined organic layers were dried, filtered and evaporated. The residue was separated by column chromatography over silica gel using a mixture of trichloromethane and methanol (97:3 by volume) as eluent. The first fraction was collected and the eluent was evaporated. The residue was crystallized from a mixture of acetonitrile and 1,1'-oxybisethane, yielding 1 part of N[[1-[(2,3-dihydro-1,4-benzodioxin-2-yl)methyl]-4-piperidinyl]methyl]-N-methyl-2-benzothiazolamine; mp. 125.4° C. (compound 62).

EXAMPLE 33

To a stirred mixture of 1.12 parts of 2-furancarboxylic acid, 2.02 parts of N,N-diethylethanamine and 195 parts of dichloromethane were added 2.55 parts of 2-chloro-1-methylpyridinium iodide. Stirring was continued for 30 minutes at room temperature. A solution of 3.93 parts of N-[1-[(2,3-dihydro-1,4-benzodioxin-2-yl)methyl]-4-piperidinylmethyl]-2-benzothiazolamine in tetrahydrofuran was added and the whole was stirred first for 1 hour at room temperature and then overnight at reflux. After cooling, the reaction mixture was poured into water. The product was extracted with dichloromethane. The extract was dried, filtered and evaporated. The residue was purified by column chromatography over silica gel using a mixture of trichloromethane and methanol, saturated with ammonia, (97:3 by volume) as eluent. The pure fractions were collected and the eluent was evaporated. The residue was converted into the hydrochloride salt in 2-propanone. The salt was filtered off and dried, yielding 2.2 parts (41.8%) of N-(2-benzothiazolyl)-N-[[1-[(2,3-dihydro-1,4-benzodioxin-2-yl)methyl]-4-piperidinyl]methyl]-2-furancarboxamide monohydrochloride; mp. 217.7° C. (compound 63).

In a similar manner there were also prepared:
N-(2-benzothiazolyl)-N-[[1-[(2,3-dihydro-1,4-benzodioxin-2-yl)methyl]-4-piperidinyl]methyl]-4-methoxybenzamide; mp. 125.6° C. (compound 64);
N-(2-benzothiazolyl)-N-[[1-[(2,3-dihydro-1,4-benzodioxin-2-yl)methyl]-4-piperidinyl]methyl]-4-(trifluoromethyl)benzamide; mp. 147.0° C. (compound 65);
N-(2-benzothiazolyl)-N-[[1-[(2,3-dihydro-1,4-benzodioxin-2-yl)methyl]-4-piperidinyl]methyl]-3,4-dimethoxybenzamide; mp. 135.0° C. (compound 66); and
N-(2-benzothiazolyl)-N-[[1-[(2,3-dihydro-1,4-benzodioxin-2-yl)methyl]-4-piperidinyl]methyl]-2-thiazolecarboxamide; mp. 125.8° C. (compound 67).

EXAMPLE 34

To a stirred mixture of 8.3 parts of N-[[1-[(2,3-dihydro-1,4-benzodioxin-2-yl)methyl]-4-piperidinyl]methyl]-N'-(4-methoxyphenyl)thiourea, 60 parts of trichloromethane and 240 parts of tetrachloromethane were added at once 3.1 parts of bromine. The whole was stirred and refluxed for 1 hour. After cooling, the reaction mixture was treated with a sodium hydroxide solution. The organic layer was separated, dried, filtered and evaporated. The residue was purified by column chromatography over silica gel using a mixture of trichloromethane and methanol (95:5 by volume) as eluent. The pure fractions were collected and the eluent was evaporated. The residue was crystallized from a mixture of 1,1'-oxybisethane and 2,2'-oxybispropane. The product was filtered off and dried, yielding 1.7 parts (21.0%) of N-[[1-[(2,3-dihydro-1,4-benzodioxin-2-yl)methyl]-4-piperidinyl]methyl]-6-methoxy-2-benzothiazolamine; mp. 134.7° C. (compound 68).

C.

PHARMACOLOGICAL EXAMPLES

EXAMPLE 35

Loss of righting reflux test

Female Wistar strain rats weighing 220–270 g were used throughout the test. Sixty minutes before observations were made, the rats were treated with a test compound or with a saline solution. Thirty minutes later, all animals received an intraperitoneal injection of 20 mg/kg body weight of xylazine. Thirty minutes after the injection of xylazine, saline pretreated (control) animals typically were in a state in which locomotor activity and other behaviours were depressed or abolished, muscle tone was decreased, and the righting reflex was compromised in the manner detailed below. The degree of which the righting reflex was compromised, was scored 0–3 depending on the animal's response to it being put gently on its back on a flat surface. Score 3: complete loss of righting reflexes; score 2: some righting movements occur, but these fail to result in a 180° turn of the body; score 1: righting movements do result in a 180° turn of the body, but the process takes noticeably more time than it does in normal animals; score 0: righting is effected with a speed similar to that of normal rats. $ED_{50}$-values were determined as those doses in mg per kg body weight capable of producing loss of righting reflex scores <3 in 50% of the tested animals.

The $ED_{50}$-values of a number of compounds of formula (I) are depicted in the table below. The compounds in this table are not given for the purpose of limiting the invention thereto but only to exemplify the useful farmacological properties of all the compounds within the scope of formula (I).

TABLE V

| Compound No. | Loss in righting reflex induced by xylazine $ED_{50}$-values in mg/kg |
|---|---|
| 1 | 0.30 |
| 6 | 0.11 |
| 7 | 1.3 |
| 8 | 0.08 |
| 19 | 0.31 |
| 20 | 0.066 |
| 21 | 0.14 |
| 58 | 0.080 |
| 68 | 0.16 |
| 13 | 0.08 |
| 42 | 0.31 |
| 57 | 0.31 |
| 34 | 0.31 |
| 26 | 0.08 |
| 27 | 0.16 |
| 35 | 0.31 |
| 28 | 0.31 |
| 30 | 0.31 |

(D)

COMPOSITION EXAMPLES

The following formulations exemplify typical pharmaceutical compositions in dosage unit from suitable for systemic administration to animal and human subjects in accordance with the instant invention.

"Active ingredient" (A.I.) as used throughout these examples relates to a compound of formula (I) or a pharmaceutically acceptable acid addition salt thereof.

EXAMPLE 36

ORAL DROPS

500 Grams of the A.I. was dissolved in 0.5 liters of 2-hydroxypropanoic acid and 1.5 liters of the polyethylene glycol at 60°~80° C. After cooling to 30°~40° C. there were added 35 liters of polyethylene glycol and the mixture was stirred well. Then there was added a solution of 1750 grams of sodium saccharin in 2.5 liters of purified water and while stirring there were added 2.5 liters of cocoa flavor and polyethylene glycol q.s. to a volume of 50 liters, providing an oral drop solution comprising 10 milligrams of the A.I. per milliliter. The resulting solution was filled into suitable containers.

EXAMPLE 37

ORAL SOLUTION

9 Grams of methyl 4-hydroxybenzoate and 1 gram of propyl 4-hydroxybenzoate were dissolved in 4 liters of boiling purified water. In 3 liters of this solution were dissolved first 10 grams of 2,3-dihydroxybutanedioic acid and thereafter 20 grams of the A.I. The latter solution was combined with the remaining part of the former solution and 12 liters 1,2,3-propanetriol and 3 liters of sorbitol 70% solution were added thereto. 40 Grams of sodium saccharin were dissolved in 0.5 liters of water and 2 milliliters of raspberry and 2 milliliters of gooseberry essence were added. The latter solution was combined with the former, water was added q.s. to a volume of 20 liters providing an oral solution comprising 20 milligrams of the active ingredient per teaspoonful (5 milliliters). The resulting solution was filled in suitable containers.

EXAMPLE 38

CAPSULES

20 Grams of the A.I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelating capsules, comprising each 20 milligrams of the active ingredient.

EXAMPLE 39

FILM-COATED TABLETS

Preparation of tablet core

A mixture of 100 grams of the A.I., 570 grams lactose and 200 grams starch was mixed well and thereafter humidified with a solution of 5 grams sodium dodecyl sulfate and 10 grams polyvinylpyrrolidone (Kollidon-K 90 ®) in about 200 milliliters of water. The wet powder mixture was sieved, dried and sieved again. Then there was added 100 grams microcrystalline cellulose (Avicel ®) and 15 grams hydrogenated vegetable oil (Sterotex ®). The whole was mixed well and compressed into tablets, giving 10.000 tablets, each containing 10 milligrams of the active ingredient.

Coating

To a solution of 10 grams methyl cellulose (Methocel 60 HG ®) in 75 milliliters of denatured ethanol there was added a solution of 5 grams of ethyl cellulose (Ethocel 22 cps ®) in 150 milliliters of dichloromethane. Then there were added 75 milliliters of dichloromethane and 2.5 milliliters 1,2,3-propanetriol. 10 Grams of polyethylene glycol was molten and dissolved in 75 milliliters of dichloromethane. The latter solution was added to the former and then there were added 2.5 grams of magnesium octadecanoate. 5 grams of polyvinylpyrrolidone and 30 milliliters of concentrated colour suspension (Opaspray K-1-2109 ®) and the whole was homogenated. The tablet cores were coated with the thus obtained mixture in a coating apparatus.

EXAMPLE 40

INJECTABLE SOLUTION 1.8 Grams methyl 4-hydroxybenzoate and 0.2 grams propyl 4-hydroxybenzoate were dissolved in about 0.5 liters of boiling water for injection. After cooling to about 50° C. there were added while stirring 4 grams lactic acid, 0.05 grams propylene glycol and 4 grams of the A.I. The solution was cooled to room temperature and supplemented with water for injection q.s. ad 1 liter volume, giving a solution of 4 milligrams A.I. per milliliters. The solution was sterilized by filtration (U.S.P. XVII p. 811) and filled in sterile containers.

EXAMPLE 41

SUPPOSITORIES

3 Grams A.I. was dissolved in a solution of 3 grams 2,3-dihydroxybutanedioic acid in 25 milliliters polyethylene glycol400. 12 Grams surfactant (SPAN ®) and triglycerides (Witepsol 555 ®) q.s. ad 300 grams were molten together. The latter mixture was mixed well with the former solution. The thus obtained mixture was poured into moulds at a temperature of 37°~38° C. to form 100 suppositories each containing 30 milligrams of the active ingredient.

What we claim is:

1. A chemical compound having the formula

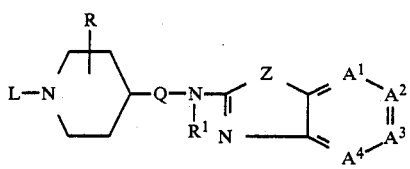

or a pharmaceutically acceptable acid addition salt or a possible stereochemically isomeric form thereof, wherein $=A^1-A^2=A^3-A^4=$ is a bivalent radical having the formula

 (f)

or

 (g)

wherein one or two hydrogen atoms in said radicals (f)-(g) may each independently from each other be replaced by halo, hydroxy, amino, trifluoromethyl, $C_{1-6}$alkyl or $C_{1-6}$alkyloxy;

Z is —O— or —S—;

$R^1$ is a member selected from the group consisting of hydrogen, $C_{1-6}$alkyl, $C_{1-6}$alkylcarbonyl, aryl $C_{1-6}$alkyl, arylcarbonyl and $C_{1-6}$-alkyloxycarbonyl;

Q is $C_{1-4}$alkanediyl;

R is a member selected from the group consisting of hydrogen, $C_{1-6}$alkyl, hydroxy and $C_{1-6}$alkyloxy;

L is a member selected from the group consisting of a radical of formula

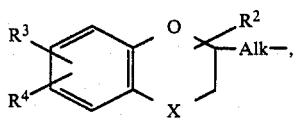 (h)

and a radical of formula

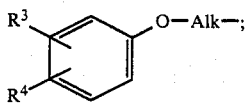 (i)

Alk is $C_{1-4}$alkanediyl;

X is —O— or —CH$_2$—;

$R^2$ is hydrogen or $C_{1-6}$alkyl;

$R^3$ and $R^4$ are each independently selected from the group consisting of hydrogen, halo, trifluoromethyl, hydroxy, $C_{1-6}$alkyl, $C_{1-6}$alkyloxy and phenyl $C_{1-6}$alkyloxy;

wherein aryl is a member selected from the group consisting of phenyl, substituted phenyl, pyridinyl, mono- and di($C_{1-6}$-alkyloxy)pyridinyl, thienyl, halothienyl, $C_{1-6}$alkylthienyl, pyrrolyl, $C_{1-6}$alkylpyrrolyl, furanyl, furanyl substituted with $C_{1-6}$alkyl, pyrazinyl, thiazolyl and imidazolyl; and substituted phenyl being phenyl substituted with up to 3 substituents each independently selected from the group consisting of halo, hydroxy, trifluoromethyl, $C_{1-6}$alkyl and $C_{1-6}$alkyloxy.

2. A chemical compound according to claim 1, wherein L is a radical of formula (h) wherein $R^3$ and $R^4$ are both hydrogen; or L is a radical of formula (i) wherein $R^3$ is hydrogen, halo, $C_{1-6}$alkyl, $C_{1-6}$alkyloxy or phenyl $C_{1-6}$alkyloxy and $R^4$ is hydrogen, halo or $C_{1-6}$alkyloxy.

3. A chemical compound according to claim 2, wherein R is hydrogen; L is a radical of formula (h) wherein $R^2$ is hydrogen, or L is a radical of formula (i) wherein $R^3$ is hydrogen or halo and $R^4$ is hydrogen; and $R^1$ is a member selected from the group consisting of hydrogen, $C_{1-6}$alkyl, $C_{1-6}$alkylcarbonyl, aryl $C_{1-6}$alkyl and arylcarbonyl.

4. A chemical compound according to claim 3, wherein Q is $C_{1-3}$alkanediyl; L is a radical of formula (h) wherein Alk is methylene; and $R^1$ is a member selected from the group consisting of hydrogen, $C_{1-4}$alkyl, aryl $C_{1-2}$alkyl and arylcarbonyl, wherein aryl is a member selected from the group consisting of phenyl, substituted phenyl, furanyl and thiazolyl; said substituted phenyl being phenyl substituted with up to 2 substituents each independently selected from the group consisting of halo, hydroxy, trifluoromethyl, methyl and methoxy.

5. A chemical compound according to claim 1 wherein said compound is:
$N^2$-[[1-[(2,3-dihydro-1,4-benzodioxin-2-yl) methyl]4-piperidinyl]methyl]thiazolo[5,4-d]pyrimidine-2,7-diamine.

6. A chemical compound according to claim 1, wherein Z is —O—.

7. A chemical compound according to claim 1, wherein Z is —S—.

8. A chemical compound according to claim 1, wherein X is —O—.

9. A chemical compound according to claim 1, wherein X is —CH$_2$—.

10. A chemical compound according to claim 1, wherein said pharmaceutically acceptable acid addition salt is a salt formed with an acid selected from the group consisting of hydrochloric, hydrobromic, sulfuric, nitric, phosphoric, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, benzoic, 2-hydroxybenzoic, 3-phenyl-2-propenoic, α-hydroxybenzeneacetic and 4-amino-2-hydroxybenzoic.

11. A chemical compound according to claim 1, wherein $=A^1-A^2=A^3-A^4=$ is a bivalent radical of formula (f).

12. A chemical compound according to claim 1, wherein $=A^1-A^2=A^3-A^4=$ is a bivalent radical of formula (g).

13. A pharmaceutical composition comprising an inert carrier and a anti-depressive or anti-Parkinson or enterokinetically effective amount of a compound having the formula

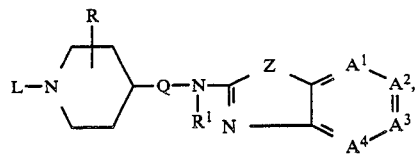 (I)

or a pharmaceutically acceptable acid addition salt or a possible stereochemically isomeric form thereof, wherein =A$^1$—A$^2$=A$^3$—A$^4$= is a bivalent radical having the formula

 (f)

or

 (g), wherein one or two hydrogen atoms in said radicals (f)-(g) may each independently from each other be replaced by halo, hydroxy, amino, trifluoromethoxy, C$_{1-6}$alkyl or C$_{1-6}$alkyloxy;

Z is —O— or —S—;

R$^1$ is a member selected from the group consisting of hydrogen, C$_{1-6}$alkyl, C$_{1-6}$alkylcarbonyl, aryl C$_{1-6}$alkyl, arylcarbonyl and C$_{1-6}$alkyloxycarbonyl;

Q is C$_{1-4}$alkanediyl;

R is a member selected from the group consisting of hydrogen, C$_{1-6}$alkyl, hydroxy and C$_{1-6}$alkyloxy;

L is a member selected from the group consisting of a radical of formula

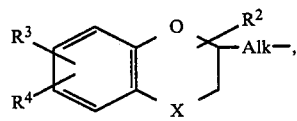 (h)

and a radical of formula

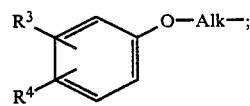 (i)

Alk is C$_{1-4}$alkanediyl;

X is —O— or —CH$_2$—;

R$^2$ is hydrogen or C$_{1-6}$alkyl;

R$^3$ and R$^4$ are each independently selected from the group consisting of hydrogen, halo, trifluoromethyl, hydroxy, C$_{1-6}$alkyl, C$_{1-6}$alkyloxy and phenyl C$_{1-6}$alkyloxy;

wherein aryl is a member selected from the group consisting of phenyl, substituted phenyl, pyridinyl, mono- and di(C$_{1-6}$alkyloxy)pyridinyl, thienyl, halothienyl, C$_{1-6}$alkylthienyl, pyrrolyl, C$_{1-6}$alkylpyrrolyl, furanyl, furanyl substituted with C$_{1-6}$alkyl, pyrazinyl, thiazolyl and imidazolyl; said substituted phenyl being phenyl substituted with up to 3 substituents each independently selected from the group consisting of halo, hydroxy, trifluoromethyl, C$_{1-6}$alkyl and C$_{1-6}$alkyloxy.

14. A pharmaceutical composition according to claim 13, wherein L is a radical of formula (h) wherein R$^3$ and R$^4$ are both hydrogen; or L is a radical of formula (i) wherein R$^3$ is hydrogen, halo, C$_{1-6}$alkyl, C$_{1-6}$alkyloxy or phenyl C$_{1-6}$alkyloxy and R$^4$ is hydrogen, halo or C$_{1-6}$alkyloxy.

15. A pharmaceutical composition according to claim 14, wherein R is hydrogen; L is a radical of formula (h) wherein R$^2$ is hydrogen, or L is a radical of formula (i) wherein R$^3$ is hydrogen or halo and R$^4$ is hydrogen; and R$^1$ is a member selected from the group consisting of hydrogen, C$_{1-6}$alkyl, C$_{1-6}$alkylcarbonyl, aryl C$_{1-6}$alkyl and arylcarbonyl.

16. A pharmaceutical composition according to claim 15, wherein Q is C$_{1-3}$alkanediyl; L is a radical of formula (h) wherein Alk is methylene; and R$^1$ is a member selected from the group consisting of hydrogen, C$_{1-4}$alkyl, aryl C$_{1-2}$alkyl and arylcarbonyl, wherein aryl is a member selected from the group consisting of phenyl, substituted phenyl, furanyl and thiazolyl; said substituted phenyl being phenyl substituted with up to 2 substituents each independently selected from the group consisting of halo, hydroxy, trifluoromethyl, methyl and methoxy.

17. A method of treating depressive conditions, Parkinson's disease or diseases related with disturbed enterokinesia in warm blooded animals suffering from the same, which method comprises the systemic administration to warm blooded animals of an effective antidepressive or anti-Parkinson or enterokinetically effective amount of a compound having the formula

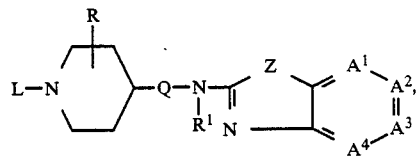 (I)

or a pharmaceutically acceptable acid addition salt or a possible stereochemically isomeric form thereof, wherein =A$^1$—A$^2$=A$^3$—A$^4$= is a bivalent radical having the formula

| | |
|---|---|
| =CH—CH=CH—CH= | (a). |
| =N—CH=CH—CH= | (b). |
| =CH—N=CH—CH= | (c). |
| =CH—CH=N—CH= | (d). |
| =CH—CH=CH—N= | (e). |
| =N—CH=N—CH= | (f). |
| or | |
| =CH—N=CH—N= | (g) | wherein one or two hydrogen atoms in said radicals (f)-(g) may each independently from each other be replaced by halo, hydroxy, amino, trifluoromethyl, C$_{1-6}$alkyl or C$_{1-6}$alkyloxy;

Z is —O— or —S—;

$R^1$ is a member selected from the group consisting of hydrogen, $C_{1-6}$alkyl, $C_{1-6}$alkylcarbonyl, aryl $C_{1-6}$alkyl, arylcarbonyl and $C_{1-6}$alkyloxycarbonyl;

Q is $C_{1-4}$alkanediyl;

R is a member selected from the group consisting of hydrogen, $C_{1-6}$alkyl, hydroxy and $C_{1-6}$alkyloxy;

L is a member selected from the group consisting of a radical of formula

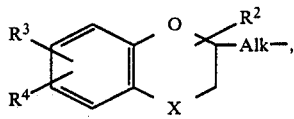
(h)

and a radical of formula

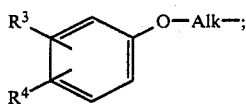
(i)

Alk is $C_{1-4}$alkanediyl;

X is —O— or —$CH_2$;

$R^2$ is hydrogen or $C_{1-6}$alkyl;

$R^3$ and $R^4$ are each independently selected from the group consisting of hydrogen, halo, trifluoromethyl, hydroxy, $C_{1-6}$alkyl, $C_{1-6}$alkyloxy and phenyl $C_{1-6}$alkyloxy;

wherein aryl is a member selected from the group consisting of phenyl, substituted phenyl, pyridinyl, mono- and di($C_{1-6}$alkyloxy)pyridinyl, thienyl, halothienyl, $C_{1-6}$alkylthienyl, pyrrolyl, $C_{1-6}$alkylpyrrolyl, furanyl, furanyl substituted with $C_{1-6}$-alkyl, pyrazinyl, thiazolyl and imidazolyl; said substituted phenyl being phenyl substituted with up to 3 substituents each independently selected from the group consisting of halo, hydroxy, trifluoromethyl, $C_{1-6}$alkyl and $C_{1-6}$alkyloxy.

18. A method according to claim 17, wherein L is a radical of formula (h) wherein $R^3$ and $R^4$ are both hydrogen; or L is a radical of formula (i) wherein $R^3$ is hydrogen, halo, $C_{1-6}$alkyl, $C_{1-6}$alkyloxy or phenyl $C_{1-6}$alkyloxy and $R^4$ is hydrogen, halo or $C_{1-6}$alkyloxy.

19. A method according to claim 18, wherein R is hydrogen; L is a radical of formula (h) wherein $R^2$ is hydrogen, or L is a radical of formula (i) wherein $R^3$ is hydrogen or halo and $R^4$ is hydrogen; and $R^1$ is a member selected from the group consisting of hydrogen, $C_{1-6}$alkyl, $C_{1-6}$alkylcarbonyl, aryl $C_{1-6}$alkyl and arylcarbonyl.

20. A method according to claim 19, wherein Q is $C_{1-3}$alkanediyl; L is a radical of formula (h) wherein Alk is methylene; and $R^1$ is a member selected from the group consisting of hydrogen, $C_{1-4}$alkyl, aryl $C_{1-2}$alkyl and arylcarbonyl, wherein aryl is a member selected from the group consisting of phenyl, substituted phenyl, furanyl and thiazolyl; said substituted phenyl being phenyl substituted with up to 2 substituents each independently selected from the group consisting of halo, hydroxy, trifluoromethyl, methyl and methoxy.

* * * * *

UNITED STATES PATENT AND TRADEMARK OFFICE
CERTIFICATE OF CORRECTION

PATENT NO. : 4,826,848

DATED : May 2, 1989

INVENTOR(S) : Frans E. Jannssen et al.

It is certified that error appears in the above-identified patent and that said Letters Patent is hereby corrected as shown below:

In Claim 13, column 35, lines 27 and 28, "other be replaced by halo, hydroxy, amino, trifluoromethoxy, $C_{1-6}$alkyl or $C_{1-6}$alkoxy;" should read --other be replaced by halo, hydroxy, amino, trifluoromethyl, $C_{1-6}$alkyl or $C_{1-6}$alkyloxy--.

In Claim 17, delete lines 49-57 in column 36. [(i.e., delete formulas (a) through (e)].

Signed and Sealed this

Sixth Day of March, 1990

Attest:

JEFFREY M. SAMUELS

*Attesting Officer*     *Acting Commissioner of Patents and Trademarks*